(12) United States Patent
Yamada et al.

(10) Patent No.: US 8,475,685 B2
(45) Date of Patent: Jul. 2, 2013

(54) PARTICLE AND NEAR-FIELD OPTICAL WAVEGUIDE

(75) Inventors: Ko Yamada, Yokohama (JP); Kenji Todori, Yokohama (JP); Shigeru Machida, Tokyo (JP)

(73) Assignees: Kabushiki Kaisha Toshiba, Tokyo (JP); Institute of National Colleges of Technology, Japan, Tokyo (JP)

( * ) Notice: Subject to any disclaimer, the term of this patent is extended or adjusted under 35 U.S.C. 154(b) by 579 days.

(21) Appl. No.: 12/722,719

(22) Filed: Mar. 12, 2010

(65) Prior Publication Data

US 2010/0239219 A1 Sep. 23, 2010

(30) Foreign Application Priority Data

Mar. 17, 2009 (JP) .................................. 2009-64835
Feb. 23, 2010 (JP) .................................. 2010-37717

(51) Int. Cl.
*H01B 1/00* (2006.01)

(52) U.S. Cl.
USPC .......................................... 252/500; 556/117

(58) Field of Classification Search
USPC ............................ 252/500; 358/130; 556/117
See application file for complete search history.

(56) References Cited

FOREIGN PATENT DOCUMENTS

| CN | 101525342 A | * | 9/2009 |
| JP | 2004-091328 A | | 3/2004 |
| JP | 2005-298496 A | | 10/2005 |
| JP | 2007148289 | | 6/2007 |
| WO | 2005109538 A3 | | 11/2005 |
| WO | 2009041365 A1 | | 4/2009 |

OTHER PUBLICATIONS

Battistini et al., "The Erratic Emission of Pyrene on Gold Nanoparticles", American Chemical Society, 2008, 2(1), pp. 77-84.*
Japanese Office Action for Japanese Patent Application No. 2010-037717 mailed on Jan. 18, 2011.
Masahiro Higuchi, et al., Stimuli Induced Structural Changes of Gold Nanoparticle Assemblies Having Sequential Alternating Amphiphilic Peptides at the Surface, Langmuir, Nov. 7, 2008, vol. 24, No. 23, pp. 13359-13363.
Japanese Office Action for Japanese Patent Application No. 2010-037717 mailed on Jun. 7, 2011.

(Continued)

*Primary Examiner* — Khanh Tuan Nguyen
(74) *Attorney, Agent, or Firm* — Turocy & Watson, LLP

(57) ABSTRACT

A particle includes: a metal; and a compound containing a hydrogen-bonding forming group, an absorption group different from the hydrogen-bonding forming group, and an aromatic ring, M representing the metal, A representing the absorption group, B representing the hydrogen-bonding forming group, a representing an integer of 0 or greater, b representing an integer of 0 or greater, c representing an integer of 1 or greater, R1 representing an aromatic ring (a planar ring up to a pi-electron number of 24) and a derivative of the aromatic ring, R2 through R5 representing a hydrogen atom, saturated hydrocarbon, unsaturated hydrocarbon, an ether bond, an ester bond, a cyano group, or derivatives of the substances and bonds, and the compound having a structure expressed by the following chemical formula.

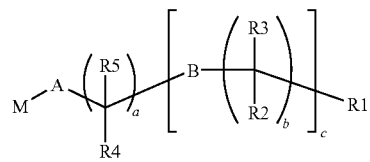

3 Claims, 27 Drawing Sheets

OTHER PUBLICATIONS

Ishihara, et al.; Review a New Dual Face Packages and Its Inkjet Copper Wiring Technology, Journal of Japan Institute of Electronics Packaging, vol. 10, No. 5, 2007, pp. 403-407.

Nakamoto; Fine Pattern Formation of Electronic Circuit by Metal and Alloy Nanoparticle Pastes, Journal of Japan Institute of Electronics Packaging, vol. 9, No. 7, 2006, pp. 533-537.

* cited by examiner

COMPOUND g

NP-a

NP-b

NP-c

NP-d

NP-e

NP-f

NP-g

SCALE 40 μm

COMPOUND p (a)

RESULTS OF FLUORESCENT MEASUREMENT OF COMPOUND p (b)

RESULTS OF FLUORESCENT MEASUREMENT OF NP-p

COMPOUND q

NP−q          NP−r

PARTICLE AND NEAR-FIELD OPTICAL WAVEGUIDE

CROSS-REFERENCE TO RELATED APPLICATION

This application is based upon and claims the benefit of priority from prior Japanese Patent Applications No. 2009-64835 and No. 2010-37717 filed on Mar. 17, 2009 and Feb. 23, 2010 in Japan respectively, the entire contents of which are incorporated herein by reference.

BACKGROUND OF THE INVENTION

1. Field of the Invention

The present invention relates to a particle and a near-field optical waveguide comprising a thin film formed with the particle.

2. Related Art

In recent years, particles (nanoparticles) having diameters of nanometer size have been synthesized by various methods, and those nanoparticles are being put into practical use. For example, JP-A 2007-148289 (KOKAI) discloses a technique for replacing electronic circuits with near-field optical waveguides of very small size exceeding the diffraction limit of light as the foundation of minute optical circuit construction. Attention is now being drawn to the nanoparticles used in the near-field optical waveguides. To use the nanoparticles to form a thin film for a waveguide, the nanoparticles may be deposited on a substrate, and etching may be performed to form a desired structure. In such a waveguide structure, however, the nanoparticles need to have quite high heat resistance.

It is known that the melting point of nanoparticles containing a metal normally becomes lower as the size of the nanoparticles becomes smaller. In view of this, a recent study has suggested that copper nanoparticles are turned into ink-like form, are applied onto a substrate, and are heated to form copper wiring. Even if the heating temperature is low, metal nanoparticles sufficiently melt to form bulk metal. Accordingly, formation of microorder wiring becomes possible (see Journals of Japan Institute of Electronic Packaging, Vol. 10, No. 5, p.p. 403-407, 2007, and Vol. 9, No. 7, p.p. 533-537, 2006, for example).

As mentioned above, the melting point becomes lower as the nanoparticles become smaller in nanometer size. Therefore, the use of those nanoparticles in the form of particles causes a problem in devices in terms of reliability in heat resistance. To counter this problem, there is a demand for rapid development of nanoparticles that have sufficient heat resistance while having a smaller nanosize diameter. By a method of forming metal wiring in an ink-jet manner with the use of nanoparticles, the organic substances are completely removed at a temperature of 250° C. Therefore, resistance to temperatures of 250° C. or higher is required. In semiconductor processing operations, 400° C. heating is often performed during the manufacturing procedures. To be used in such a semiconductor circuit, a near-field optical waveguide needs to endure 400° C.

SUMMARY OF THE INVENTION

The present invention has been made in view of these circumstances, and an object thereof is to provide a particle having heat resistance, and a near-field optical waveguide comprising wiring formed with the particle.

A particle according to a first aspect of the present invention includes: a metal; and a compound containing a hydrogen-bonding forming group, an absorption group different from the hydrogen-bonding forming group, and an aromatic ring, M representing the metal, A representing the absorption group (a thiol group, an amino group, or a carboxyl group), B representing the hydrogen-bonding forming group (an amide-bonding group, an urea-bonding group, or a derivative of those groups, or a structure containing at least one of a thiol group, an amino group, a carbonyl group, a carboxyl group, and a hydroxyl group, or a derivative of the groups), a representing an integer of 0 or greater, b representing an integer of 0 or greater, c representing an integer of 1 or greater, R1 representing an aromatic ring (a planar ring up to a pi-electron number of 24) and a derivative of the aromatic ring, R2 through R5 representing a hydrogen atom, saturated hydrocarbon, unsaturated hydrocarbon, an ether bond, an ester bond, a cyano group, or derivatives of the substances and bonds, and the compound having a structure expressed by the following chemical formula.

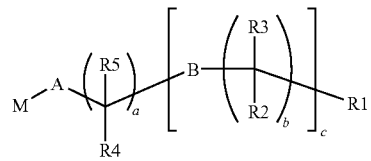

A particle according to a second aspect of the present invention includes: a metal; and a compound provided as a ligand of the gold nanoparticle, and containing a thiol group, an amide bond, and alkylene, or containing a thiol group, carboxylato, and alkylene in a molecule.

A near-field optical waveguide according to a third aspect of the present invention includes: a supporting substrate; and a particle layer including the particle of the first aspect deposited on the supporting substrate, and serving as an interconnect layer through which plasmon polariton is transmitted.

DETAILED DESCRIPTION OF THE INVENTION

Figure 1:
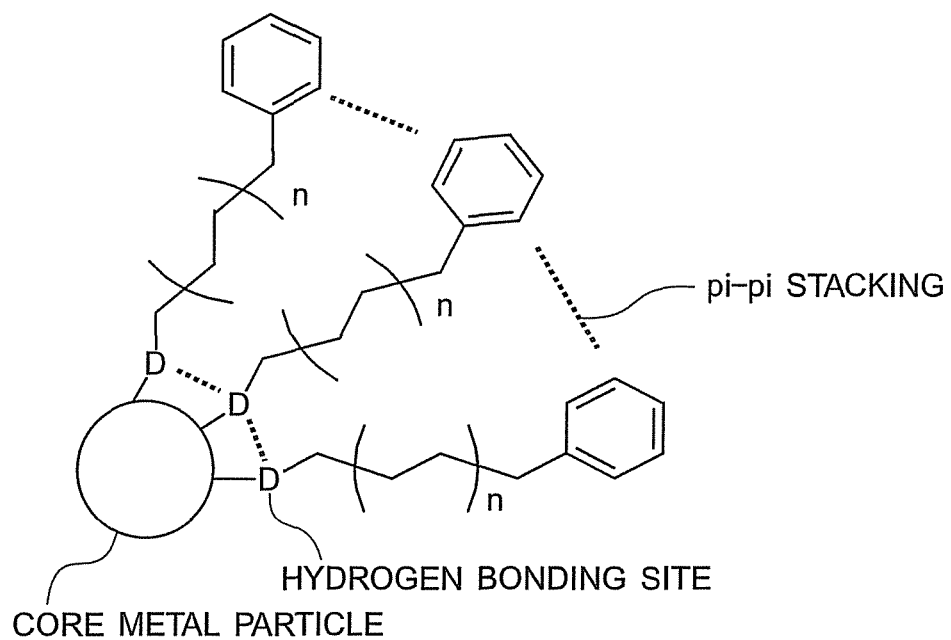
FIG. 1 is a schematic view showing an example of a core-shell nanoparticle according to an embodiment of the present invention.

The present invention is now briefly explained before embodiments of the present invention are described.

While nanoparticles exist in various forms, nanoparticles that are dispersible in organic solvents are desirable in forming a film on a substrate. Such nanoparticles also need to be in high concentration when dispersed in organic solvents. Taking those requests into consideration, the inventors selected metal nanoparticles (core-shell nanoparticles) formed with an organic substance and a metal, as the nanoparticles to be used in waveguide structures. Each core-shell nanoparticle has a nanoparticle core made of a metal at its center, and an organic substance is placed to surround the nanoparticle core through chemical bonding. In such particles, the characteristics of the organic substance become more prominent than the characteristics of the particles. Such particles can be collected as a solid like a general low-molecular compound. Even after dissolved with an organic solvent, those particles do not form secondary aggregate, and can be evenly dispersed. Also, bonding force is characteristically caused between an organic substance and the metal atoms in the surface of a metal particle. Where gold is selected as the core metal particle, and a thiol compound is selected as the organic substance, chemical bonding is caused between the gold atoms in the core surface and the sulfur atoms in the thiol compound.

In a core-shell nanoparticle of the above form, the dispersibility in a solvent is determined by the shell of the organic substance, and the solubility can be easily increased accordingly. Such particles are applied and deposited onto a substrate, and are processed into a waveguide form to be put into practical use. At this point, each metal portion serving as a core of nanoparticles is shielded by the organic substance forming the shell. By maintaining this form, the function as a near-field optical waveguide of plasmon polariton type can be obtained.

However, the chemical bonding between the metal atoms and the sulfur atoms in the thiol compound is cut off by heating, and core metal particles are welded to one another and turn into a bulk structure. This phenomenon occurs at relatively low temperatures of 100° C. to 200° C. By taking advantage of this principle, electric conduction wiring formation of ink-jet type has been suggested (see Journals of Japan Institute of Electronic Packaging, Vol. 10, No. 5, p.p. 403-407, 2007, and Vol. 9, No. 7, p.p. 533-537, 2006).

This phenomenon hinders the formation and shape maintenance of a near-field optical waveguide structure according to an embodiment of the present invention. Since a heating process needs to be carried out to produce a waveguide, processing cannot be performed, and the reliability in heat resistance of the product might be degraded, unless the nanoparticles have sufficient heat resistance.

To counter the above particular problems, the inventors paid attention to the interactions between organic molecules forming the shell of each core-shell nanoparticle. In such a core-shell nanoparticle, organic molecules are bonded to one another in the surface of the core metal particle. By intensifying the interactions between the organic molecules, the organic molecules are prevented from coming off the metal particle. The organic molecules form basket-like bonding, to firmly surround the core metal particle. The heat resistance is made higher by virtue of this effect.

However, it is difficult to cause covalent bonding with the strongest bonding force between molecules. Covalent bonding may be caused only by photo polymerization. In doing so, however, bonding is caused not only between the organic molecules placed around the metal particles, but also between the metal particles. As a result, the solubility is greatly reduced. The second strongest bonding is ion bonding. However, ionic molecules are easily crystallized, and only have a weak affinity for organic solvents. These properties hinder film formation.

To cause bonding among the organic molecules surrounding core metals in a simpler and more certain manner, hydrogen bonding might be used. Therefore, hydrogen bonding is caused by introducing O atoms of amide and N atoms into the organic substance in an embodiment of the present invention. The N—H portions and C—O portions form hydrogen bonds with N and O of the neighboring molecules, and achieve stability. However, sufficient interactions are not obtained through the hydrogen bonding. The bonding force of one hydrogen bond is approximately 20 kJ/mol, which is less than a tenth of the bonding force of a carbon bond as a general covalent bond, which is approximately 840 kJ/mol. To achieve sufficient bonding force, factors to form hydrogen bonds may be created, so as to increase the bonding force. In doing so, however, the molecules become linearly longer, and, when a waveguide is formed with a thin film, the metal particles as the cores of the nanoparticles become further apart from one another. This might lower the waveguide efficiency. If the core metal particles become further apart from one another, the waveguide loss of incident light becomes larger. This can be easily predicted from the principles of plasmon light propagation on the surfaces of metal particles disclosed in JP-A 2007-148289 (KOKAI). Therefore, increasing the number of hydrogen bonds by increasing the molecular length is not preferred.

As another bonding means, interactions between pi-electrons are used. An aromatic ring is attached to the end of each molecule, to cause interactions between pi-electrons. By doing so, the bonding between molecules becomes stronger. The interactions between pi-electrons are the London dispersion force acting between the aromatic rings, and the bonding force thereof is much smaller than the bonding force of hydrogen bonds. However, if there is an environment that facilitates bonding between pi-electrons, even weak interactions can generate a great bonding effect. For example, in a discotic-type liquid crystal, molecules are arranged in a regular array by virtue of the bonding between pi-electrons. This is also one of the essential factors in stabilizing three-dimensional molecular shapes in a protein substance. Accordingly, if there is a three-dimensional environment prepared for interactions between pi-electrodes, the interactions between pi-electrons have a sufficient energy for arrangement with certain regularity.

Figure 25:
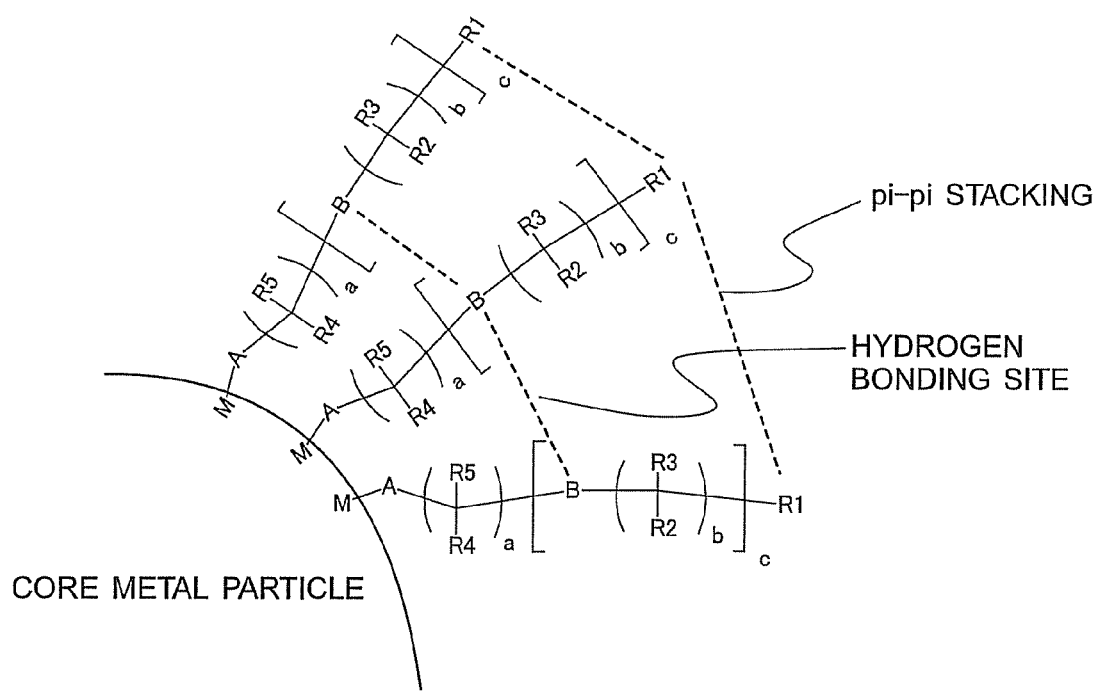
FIG. 25 is a schematic view showing a specific example of a compound that is bound to a metal particle to be a core.

In a core-shell nanoparticle of an embodiment of the present invention, hydrogen bonds are formed in the ligand of the core metal particle, and aromatic rings are provided at the outer most portion, to create an environment in which aromatic rings are easily arranged, and interactions are caused between pi-electrons. FIG. 1 is a schematic view showing this arrangement. In FIG. 1, "D" represents hydrogen bonding site. FIG. 25 shows a specific example of a compound that is bound to a metal particle to be a core. This compound is expressed by the following formula:

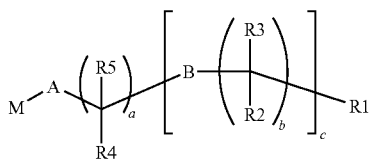

Here, M represents the substance forming the metal, A represents the absorption group (a thiol group, an amino group, or a carboxyl group), B represents the hydrogen-bonding forming group (an amide group, a urea group, or a derivative of those groups, or a structure containing one or more of a thiol group, an amino group, a carbonyl group, a carboxyl group, and a hydroxyl group, or a derivative of those groups), a represents an integer of 0 or greater, b represents an integer of 0 or greater, c represents an integer of 1 or greater, R1 represents an aromatic ring (a planar ring up to a pi-electron number of 24) and a derivative of this aromatic ring, and R2 through R5 represent a hydrogen atom, saturated hydrocarbon, unsaturated hydrocarbon, an ether bond, an ester bond, a cyano group, or derivatives of those substances and bonds. By this technique, bonds between pi-electrons were effectively formed, and a greater increase in heat resistance was realized than in the cases of molecules only having hydrogen bonds.

While various kinds of hydrogen-bonding groups may be considered, the terms that are not clear in this specification are now defined. According to the Encyclopedia of Chemistry (Kyoritsu Shuppan Co., Ltd.), "amide" is "the name of a group in which an amino group-$NH_2$ is bound to an acid group to form a RCONH-structure". Also, "urea" is expressed as ($H_2N$—CO—$NH_2$). Meanwhile, "amine" is "a compound obtained by substituting the hydrogen atoms of ammonia with a hydrocarbon residue". Accordingly, amide and urea can be regarded as part of amine. In this specification, however, amide groups each have an amide structure (—NH—CO—), and urea groups each have a urea structure (—NH—CO—NH—). Therefore, amide-bonding groups and urea-bonding groups are described as different concepts from amine and amino groups. Likewise, amide and urea are explained as different concepts from carbonyl and carbonyl groups.

In the above description, hydrogen-bonding forming groups are limited to amide in the explanation of the energy relationship. However, hydrogen-bonding forming groups are not limited to amide. In amide, the C=O link and the N—H link are adjacent to each other, and continuous hydrogen bonds can be formed over a large number of molecules. Therefore, the use of amide is desirable. However, the same effects can be achieved with urea-bonding groups. The molecules are arranged in a straight chain, and the aromatic rings that cause pi-pi stacking exist at the end of the molecules. With this being taken into consideration, the occupied volume should preferably be small, so that a high degree of freedom is allowed for bonding, and continuous hydrogen bondings can be formed at sites close to particles. Therefore, the use of amide is most preferred. It is also possible to use thiol groups, amino groups, carbonyl groups, carboxyl groups, hydroxyl groups, and the likes, though their effects are not as strong as the effects of amide.

FIG. 2(a) through 2(f) show compounds (long-chain alkanethiol derivatives) used as ligands in the embodiment of the present invention. The chemical formulas of FIGS. 2(a) through 2(d) represent compounds in which the carbon chain number in normal-alkylamine is 8, 12, 16, and 18. In each of those drawings, the number shown at the right lower side of the brackets indicates the number of repetitions. Each of the compounds shown in FIGS. 2(a) through 2(d) has a thiol group, an amide group, and alkylene (an alkyl group). The compound shown in FIG. 2(e) has a thiol group, carboxylato, alkylene (an alkyl group), and an aromatic ring (a tolyl group). The compound shown in FIG. 2(f) has a thiol group, an amide group, alkylene (an alkyl group), and an aromatic ring.

Figure 2:
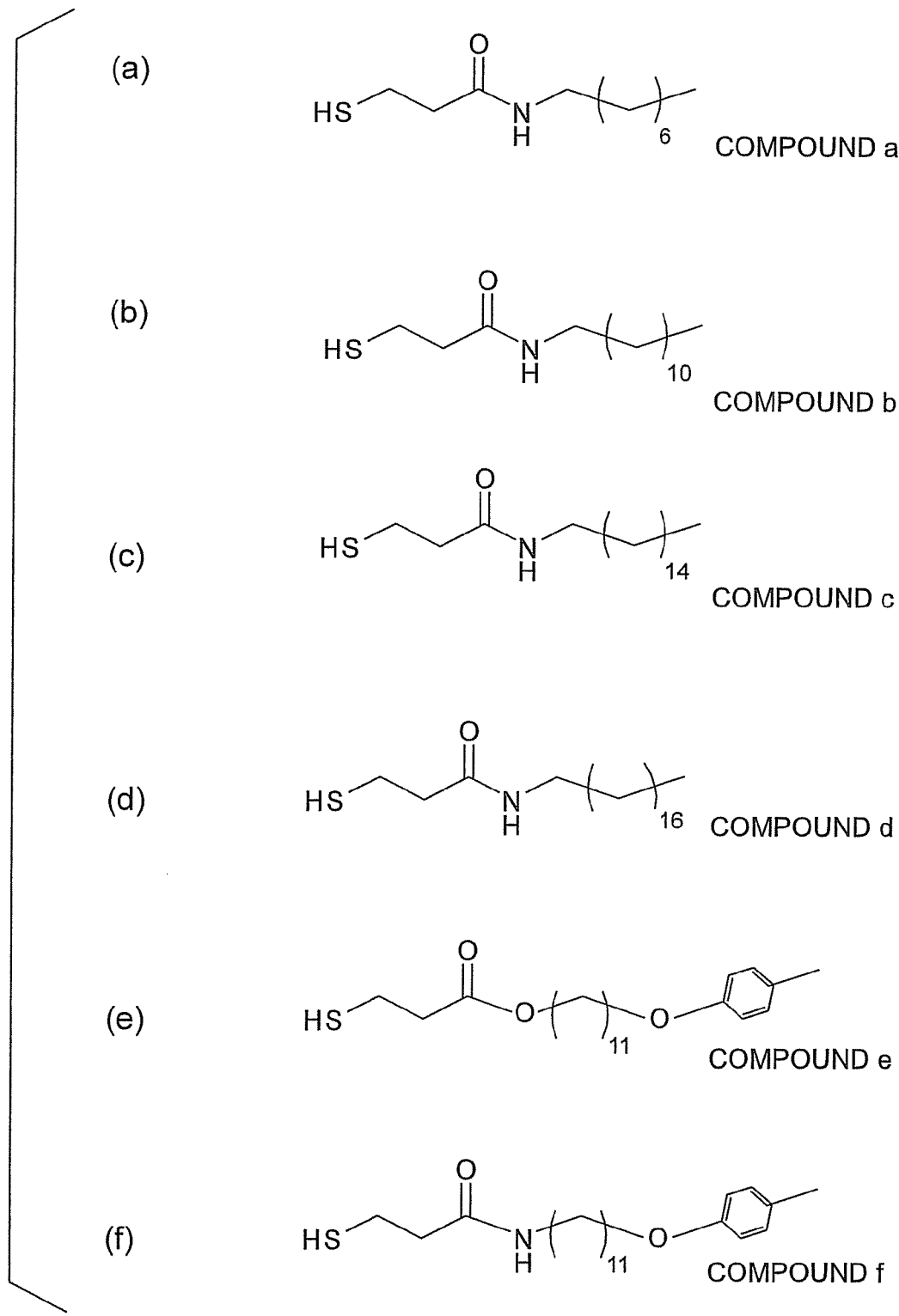
FIGS. 2(a) through 2(f) are schematic views showing specific examples of long-chain alkanethiol derivatives used as ligands in the embodiment of the present invention.
Figure 3:
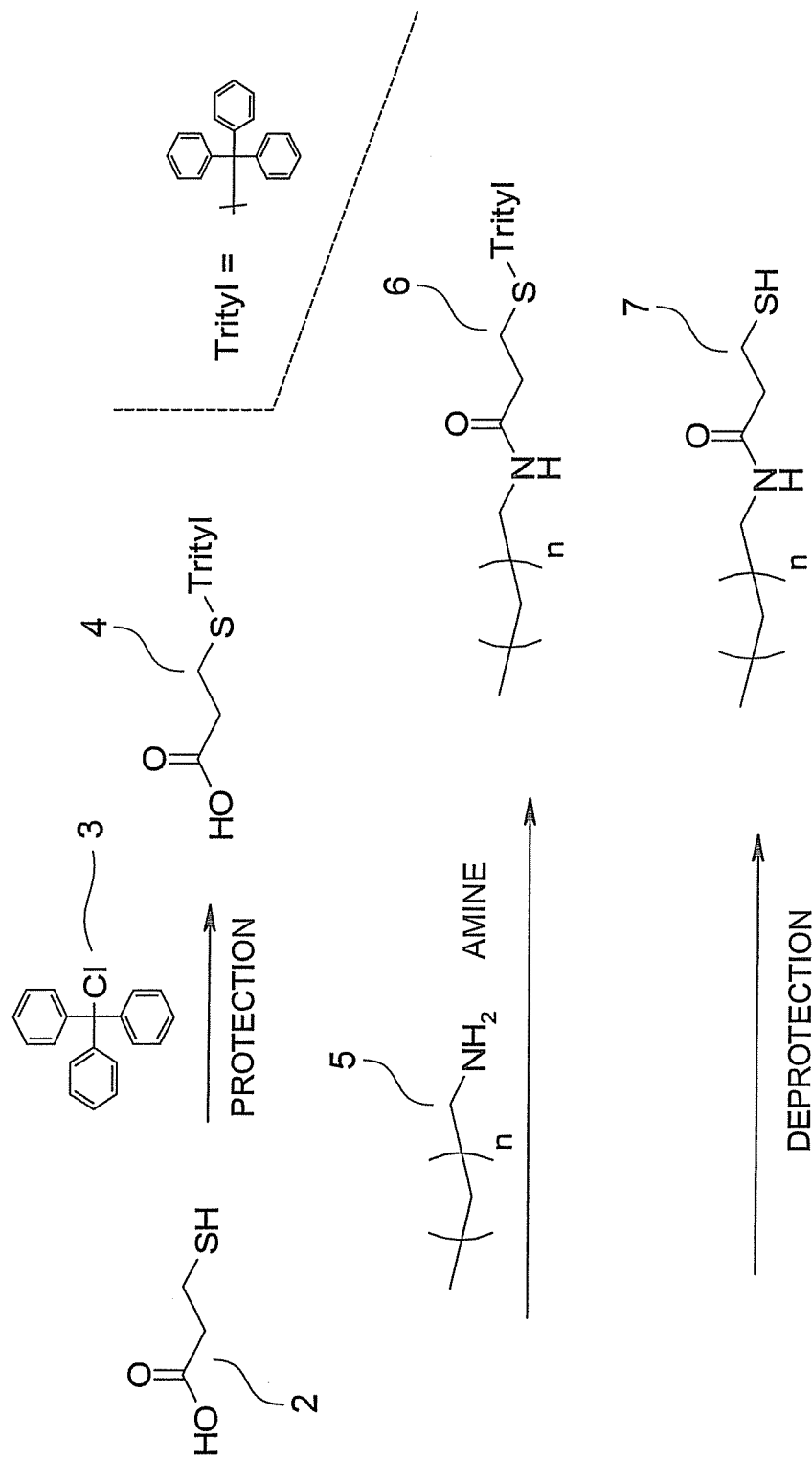
FIG. 3 is a diagram for explaining the synthesis route of the long-chain alkanethiol derivatives shown in FIGS. 2(a) through 2(d)

Referring now to FIG. 3, the method for the synthesis of the compounds shown in FIGS. 2(a) through 2(d) is described.

Synthesis of 3-(tritylthio) propanoic acid 4

Mercaptopropionic acid 2 (3.14 g) was dissolved in 50 ml of methylene chloride. Triphenylmethylchloride 3 (8.36 g, 30 mmol) was added to that, and 19-hour protection reactions were carried out at room temperature. The precipitate generated through the protection reactions was filtered and gathered, and was rinsed with 40 ml of diethyl ether. The precipitate was then dried under reduced pressure, to form 9.86 g of 3-(tritylthio)propanoic acid 4, which is a white solid.

Synthesis of N-alkyl-3-(tritylthio) propaneamide 6

After a 500-ml three-inlet flask was dried under reduced pressure, predetermined amounts of 3-(tritylthio)propanoic acid 4, 1-ethyl-3-(3-dimethylaminopropyl)carbodiimide hydrochloride (EDC), and 4-dimethylaminopyridine (DMAP) were dissolved in methylene chloride in the flask in a nitrogen atmosphere. A predetermined amount of normal-alkylamine 5 was added to that, and was stirred overnight at room temperature. The addition of the normal-alkylamine 5 was performed in each of the cases where the carbon chain number in the normal-alkylamine 5 was 8, 12, 16, and 18. Each of the reactant mixtures was washed twice with 100 ml of aqueous saturated sodium hydrogen sulfate solution, was rinsed twice with 100 ml of pure water, and was washed twice with 100 ml of saturated saline. Magnesium sulfate was then added to the organic phase (methylene chloride phase), and was dried overnight. After the desiccant agent was separated by filtration, the solvent was distilled away. In this manner, N-alkyl-3-(tritylthio)propaneamide 6, which is the objective substance, was obtained. The resultants were purified through recrystallization.

Synthesis of N-alkyl-3-mercaptopropaneamide 7
(hereinafter also referred to as the compounds a
through d)

The N-alkyl-3-(tritylthio)propaneamide 6 and trifluoroacetic acid were next introduced into a 100-ml round-bottomed flask, and were stirred to form an orange-colored uniform solution. Triethylsilane was then added to that to generate a white-colored precipitate. At this point, the solution became transparent. In this circumstance, the solvent was distilled away under reduced pressure, and the solid residue was dissolved in 100 ml of methylene chloride and was washed with 100 ml of aqueous saturated sodium hydrogen carbonate solution. After the methylene chloride phase was dehydrated with magnesium sulfate, the solvent was distilled away under reduced pressure. The solid residue was purified by column chromatography, to obtain N-alkyl-3-mercaptopropaneamide 7 (the compounds a through d), which is a white-colored solid. In this manner, the compound a, the compound b, the compound c, and the compound d shown in FIGS. 2(a) through 2(d) were obtained, with the carbon chain number n in the normal-alkylamine 5 being 8, 12, 16, and 18.

Figure 4:
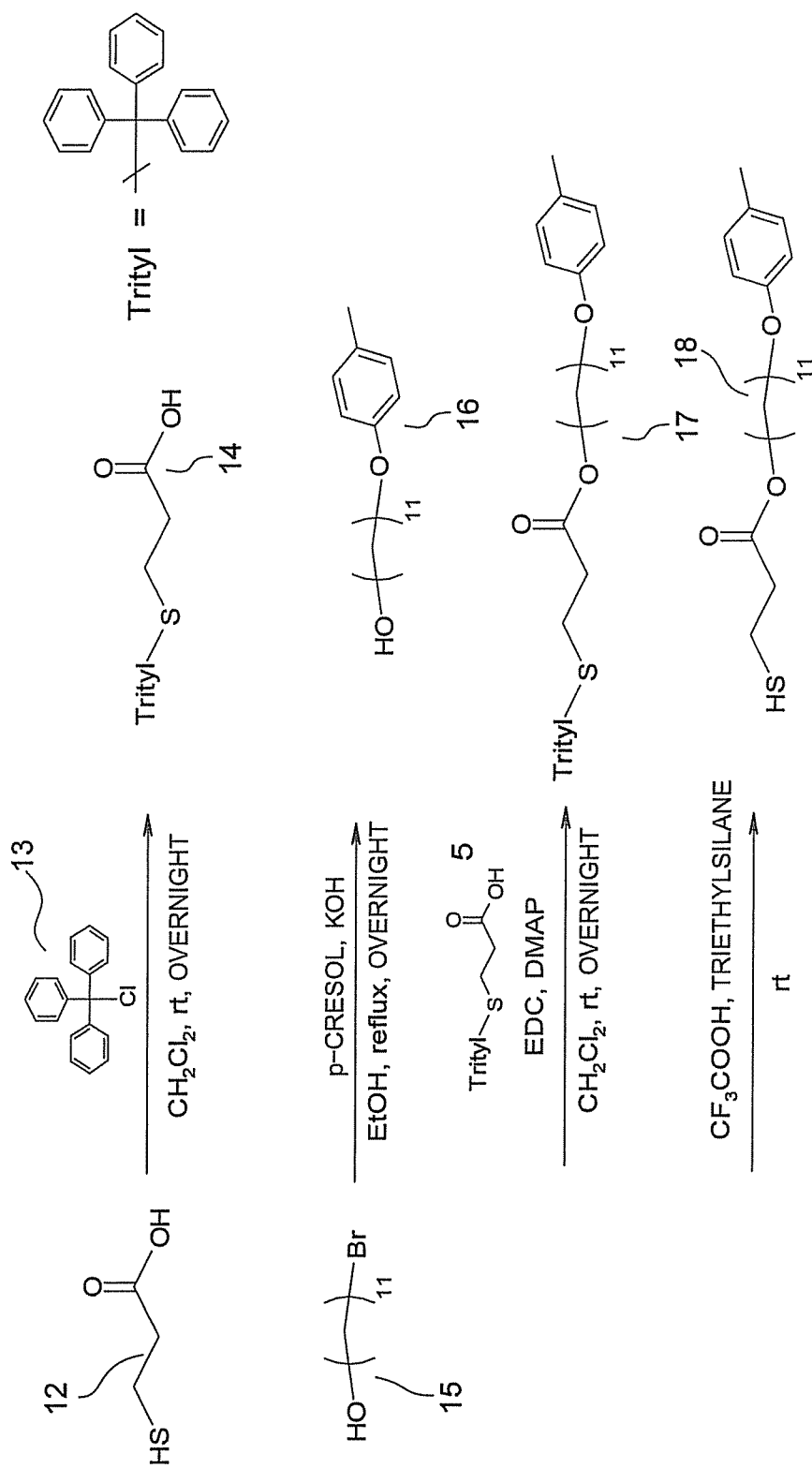
FIG. 4 is a diagram for explaining the synthesis route of the compound e shown in FIG. 2(e)

Referring now to FIG. 4, the synthesis of 3-mercaptopropionic acid 11-(para-tolyloxy)undecylester 18 (hereinafter also referred to as the compound e), which is the compound shown in FIG. 2(e) as a long-chain alkanethiol derivative used as a ligand in the embodiment of the present invention, is described. FIG. 4 is a diagram showing the synthesis route of the compound e, which is a thiol derivative having a tolyl group and ester bonds in the molecules.

Synthesis of 11-(p-tolyloxy)undecyl
3-mercaptopropioate 18 (compound e)

First, the thiol group of 3-mercaptopropionic acid was protected with a trityl group, to form a compound 14. The bromo group of a compound 15 that is 11-bromoundecane-1-ol was substituted with a tolyl group by the Williamson's ether synthesis, to form a compound 16. A compound 17 having an ester bond was then formed through a dehydration condensation reaction between the compound 14 and the compound 16. After that, the trityl group was removed through a deprotection reaction, and the compound b as the objective substance was obtained.

Synthesis of 3-(tritylthio)propionic acid 14

Mercaptopropionic acid 12 (3.14 g) was dissolved in 50 ml of methylene chloride. Triphenylmethylchloride 13 (8.36 g) was added to that, and 19-hour reactions were carried out at room temperature. The precipitate generated through the reactions was gathered by filtration, and the solid components obtained here were dried under reduced pressure, to form 9.86 g of 3-(tritylthio)propionic acid 14, which is a white solid.

Synthesis of 11-(p-tolyloxy)undecan-1-ol 16

The 11-bromoundecan-1-ol 15 (3.68 g) and 4.88 g of p-cresol were dissolved in 20 ml of ethanol, and 2.57 g of potassium hydroxide was added to that, followed by 24-hour refluxing. After cooled to room temperature, the reaction solution is moved into a separating funnel, and 100 ml of ion-exchange water and 50 ml of methylene chloride were added so as to cause separation. After the organic phase was collected and was dehydrated with sodium sulfate, the desiccant agent was removed by filtration, and the solvent of the filtrate was distilled away under reduced pressure. The resultant solid was re-dissolved in 50 ml of toluene, and was washed twice with 10 wt % of aqueous potassium hydroxide solution, and was then washed with 50 ml of saturated saline. After that, the organic phase was collected, and was dehydrated with sodium sulfate. The desiccant agent was removed by filtration, and the solvent of the filtrate was distilled away under reduced pressure, to obtain 4.08 g of 11-(p-tolyloxy)undecan-1-ol 16, which is a white solid.

Synthesis of 11-(p-tolyloxy)undecyl
3-(tritylthio)propioate 17

The compound 14 (1.86 g), 0.896 g of 1-ethyl-3-(3-dimethylaminopropyl)carbodiimide hydrochloride (EDC), and 0.029 g of 4-dimethylaminopyridine (DMAP) were dissolved in 300 ml of methylene chloride. After the compound 16 (3.04 g) was then added and stirred at room temperature for 24 hours, the reaction solution was moved into a separating funnel, and was washed twice with 100 ml of 10% aqueous potassium hydrogen sulfate solution, twice with 100 ml of aqueous saturated sodium hydrogen carbonate solution, twice with 100 ml of ion-exchange water, and twice with 100 ml of saturated brine. After the methylene chloride phase collected was dehydrated with magnesium sulfate, the desiccant agent was removed by filtration, and the solvent of the filtrate was distilled away under reduced pressure. The reaction mixture was purified by chromatography, and 2.63 g of 11-(p-tolyloxy)undecyl 3-(tritylthio)propioate 17, which was a white solid, was obtained.

Synthesis of 11-(p-tolyloxy)undecyl
3-mercaptopropioate 18 (compound e)

The compound 17 (1.11 g) was weighed and poured into a 100-ml round-bottomed flask, and 10 ml of trifluoroacetic acid was added and stirred, to obtain an orange-colored homogenous solution. After 0.9 ml of triethylsilane was added to generate a white-colored precipitate, the supernatant solution (transparent) was distilled away under reduced pressure. The solid obtained was purified by chromatography, and 0.6 g of the compound e, which was a white solid, was obtained.

Figure 5:
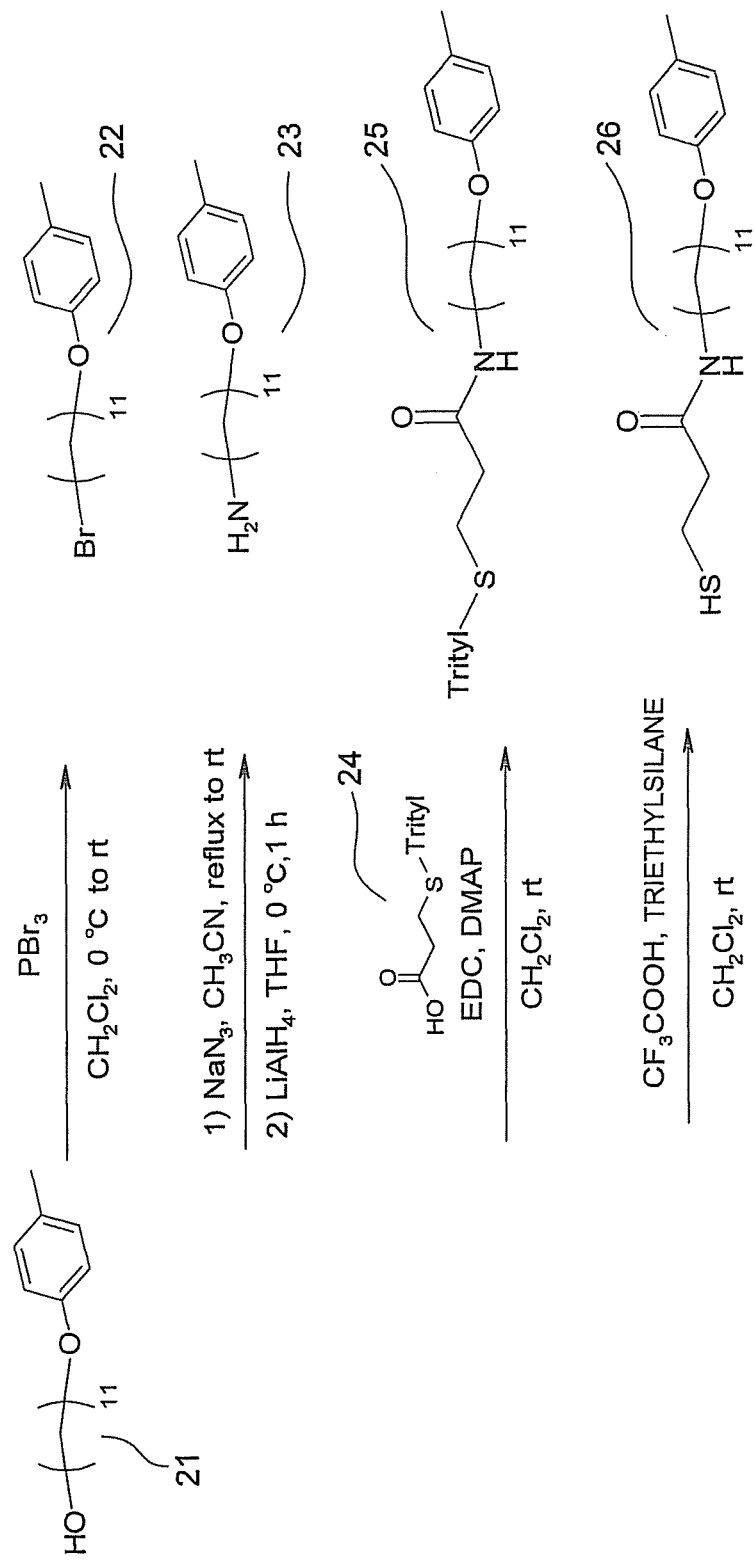
FIG. 5 is a diagram for explaining the synthesis route of the compound f shown in FIG. 2(f)

Referring now to FIG. 5, the synthesis of (N-(11-(p-tolyloxy)undecyl)-3-mercaptopropaneamide (hereinafter also referred to as the compound f), which is the compound shown in FIG. 2(f) as a long-chain alkanethiol derivative used as a ligand in the embodiment of the present invention, is described. FIG. 5 is a diagram showing the synthesis route of the compound f, which is a thiol derivative having a tolyl group and an amide group in the molecules.

Synthesis of N-(11-(p-tolyloxy)undecyl)-3-mercaptopropaneamide 26 (compound f)

The hydroxy group of a compound 21 was substituted with a bromo group by phosphorus tribromide, to form a compound 22. After the bromo group was substituted with an azido group, the resultant was reduced to an amino group by lithium aluminum hydride, to form a compound 23. The compound 23 was then reacted with a compound 24, to form a compound 25 having an amide group. After that, the trityl group was removed through a deprotection reaction, to obtain the compound f, which was the objective substance.

Synthesis of (11-bromoundecyl)tolylether 22

The compound 21 (1.31 g) was dissolved in 10 ml of methylene chloride dehydrated with molecular sieves, and was cooled in an ice bath. Phosphorus tribromide (1.70 g) dissolved in 10 ml of dried methylene chloride was dripped, and was stirred in an ice bath for four hours and at room temperature for 21 hours. After the solvent was removed by an evaporator, 30 ml of ethyl acetate was newly added to that, and the resultant was washed twice with 25 ml of pure water. After the organic phase collected was dehydrated with sodium sulfate, the desiccant agent was removed by filtration, and the solvent of the filtrate was distilled away under reduced pressure. The reaction mixture was purified by silica-gel column chromatography (the developing solvent: methylene chloride), and 0.5 g of (11-bromoundecyl)tolylether 22, which was a white solid, was obtained.

Synthesis of (11-aminoundecyl)tolylether 23

The compound 22 (0.506 g) was dissolved in 50 ml of acetonitrile. Sodium azide (0.395 g) was then added to that, and 29-hour reaction was carried out by refluxing, followed by 95-hour reaction at room temperature. After the resultant was cooled down to room temperature, the solid components were removed by filtration. The solvent of the filtrate was then distilled away under reduced pressure, and 0.313 g of a transparent, viscous liquid was obtained. This liquid was dissolved in 15 ml of THF distilled from calcium hydride in a nitrogen atmosphere, and was cooled in an ice bath. Lithium aluminum hydride (0.054 g) was then dissolved in 20 ml of dried THF, and was dripped. After the resultant was stirred in an ice bath for one hour, 80 μl of ion-exchange water, 80 of 15 wt % of aqueous potassium hydride solution, and 240 μl of ion-exchange water were added so as to stop the reaction. The precipitate generated was removed by filtration, and the solvent of the filtrate was distilled away under reduced pressure. The solid obtained was then dissolved in ethyl acetate (30 ml), and was washed twice with 30 ml of ion-exchange water. The organic phase was then collected, and was dehydrated with magnesium sulfate. The desiccant agent was removed by filtration, and the solvent of the filtrate was distilled away under reduced pressure. In this manner, 0.2 g of (11-aminoundecyl)tolylether 23, which was a white solid, was obtained.

Synthesis of N-(11-(p-tolyloxy)undecyl)-3-(tritylthio)propaneamide 25

The compound 23 (0.174 g), EDC (0.123 g), DMAP (0.009 g), and the compound 24 (0.220 g) were dissolved in 50 ml of methylene chloride, and were stirred at room temperature for 22 hours. After that, the reaction solution was moved into a separating funnel, and was washed twice with 50 ml of 10% hydrochloric acid, twice with 50 ml of aqueous saturated sodium hydrogen carbonate solution, twice with 50 ml of ion-exchange water, and 50 ml of saturated brine. After the organic phase collected was dehydrated with sodium sulfate, the desiccant agent was removed by filtration, and the solvent of the filtrate was distilled away under reduced pressure. The reaction mixture was purified by chromatography, and 0.2 g of N-(11-(p-tolyloxy)undecyl)-3-(tritylthio)propaneamide 25, which was a white solid, was obtained.

Synthesis of N-(11-(p-tolyloxy)undecyl)-3-mercaptopropaneamide 26 (compound f)

The compound 25 (0.181 g) was dissolved in 1 ml of methylene chloride, and 0.5 ml of trifluoroacetic acid was added to that while being stirred, to obtain a brown-colored solution. After a white-colored precipitate was generated by adding 0.16 ml of triethylsilane, the supernatant solution was distilled away under reduced pressure. The solid obtained was dissolved by the new addition of 20 ml of methylene chloride, and was washed twice with 30 ml of aqueous saturated sodium hydrogen carbonate solution and twice with 30 ml of saturated brine. After the collected organic phase was dehydrated with magnesium sulfate, the desiccant agent was removed by filtration, and the solvent of the filtrate was distilled away under reduced pressure. The reaction mixture was purified by chromatography, and 0.1 g of the compound f, which was a white solid, was obtained.

Next, the formation of core-shell nanoparticles having the above described compound a, compound b, compound c, compound d, compound e, and compound f as the ligands is described.

Tetraoctyl ammonium bromide (TOAB) (0.65 g) was put into a 500-ml conical flask, and was dissolved in 160 ml of toluene. A solution formed by dissolving 0.20 g of hydrogen tetrachloroaurate (III)/tetrahydrate in 60 ml of ion-exchange water was added to that, and was stirred vigorously. After the organic phase turned yellow, one of the above compounds a, b, c, d, e, and f was added to a solution formed by dissolving ½ mol of TOAB in 20 ml of toluene, and was stirred for 15 minutes. Sodium borohydride (0.23 g) was then dissolved in 60 ml of water and added to that. While being stirred vigorously at room temperature, the resultant was reacted overnight. The organic phase after the reaction was collected, and was condensed by an evaporator. While being stirred, the resultant was dripped little by little onto 100 ml of methanol, and reprecipitation of gold nanoparticles was carried out. After stirring was continued overnight, solid components were collected by filtration with the use of a filter under reduced pressure. In this manner, 0.1 g of black-colored solid was obtained in each case.

Figure 21:
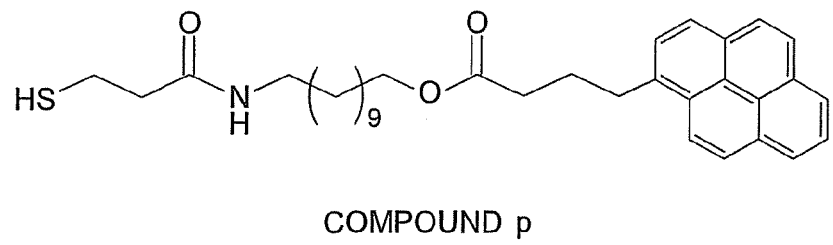
FIG. 21 is a schematic view of a compound p.
Figure 22:
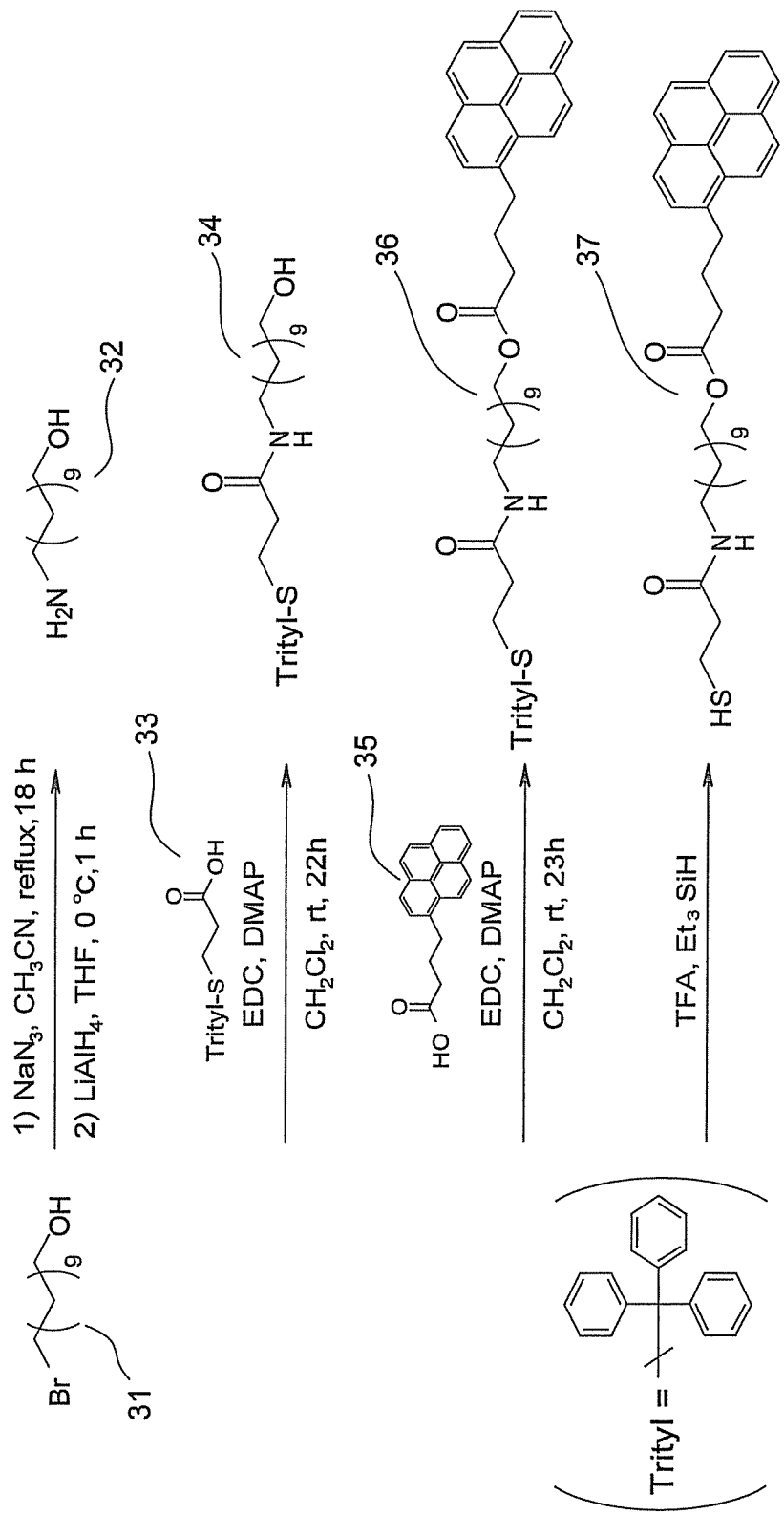
FIG. 22 is a diagram for explaining the synthesis route of the compound p.

FIG. 21 shows another example of a compound (a long-chain alkanethiol derivative) used as a ligand in the embodiment of the present invention. FIG. 22 shows a method for the synthesis of the compound. This compound p is 4-(pyrene-1-yl)butanoic acid 11-(3-mercaptopropaneamide)undecylester, and has a thiol group, an amide group, alkylene (alkyl group), carboxylato, and an aromatic ring.

Synthesis of 4-(pyrene-1-yl)butanoic acid 11-(3-mercaptopropaneamide)undecylester 37 (compound p)

As shown in FIG. 22, after the bromo group of 11-bromoundecan-1-ol 31 was substituted with an azido group through a S$_N$2 reaction, the resultant was reduced to an amino group by lithium aluminum hydride, to form a compound 32. The compound 32 was then reacted with a compound 33, to form a compound 34 having an amide group. The compound 34 and 4-(pyrene-1-yl)butanoic acid 35 were condensed through dehydration, to form an ester bond and a compound 36. After that, the trityl group was removed by a deprotection reaction, and a compound 37 (the compound p), which was the objective substance, was obtained.

The synthesis of each of the compounds 32, 34, 36, and 37 is described below in greater detail.

Synthesis of 11-aminoundecan-1-ol 32

11-bromoundecan-1-ol (the compound 31) (15.1 g) was dissolved in 250 ml of acetonitrile, and 15.7 g of sodium azide was added to that, followed by 18-hour reaction caused by refluxing. After cooled down to room temperature, the solid components were removed by filtration. The solvent of the filtrate was distilled away under reduced pressure, to obtain 13.9 g of a transparent, viscous liquid. Of this liquid, 8.34 g was dissolved in 60 ml of THF distilled from calcium hydride in a nitrogen atmosphere, and was cooled in an ice bath. Lithium aluminum hydride (2.53 g) was then dried, and was dissolved in 250 ml of THF. The resultant was dripped, and was then stirred in an ice bath for one hour. After that, 2.5 ml of ion-exchange water, 3.5 ml of 15 wt % aqueous sodium hydride solution, and 7.5 ml of ion-exchange water were added so as to stop reactions. The precipitate generated was removed by filtration, and the solvent of the filtrate was distilled away under reduced pressure. After the filtrate was dried under reduced pressure, the dried filtrate was dissolved in 60 ml of THF, and the same volume of heptane was added to that. The precipitate generated was collected by filtration, to obtain 5.1 g of a white solid 32.

Synthesis of N-(11-hydroxyundecyl)-3-(tritylthio)propaneamide 34

The compound 33 (2.44 g), 1.35 g of 1-ethyl-3-(3-dimethylaminopropyl)carbodiimide hydrochloride, and 0.09 g of 4-dimethylaminopyridine were dissolved in 100 ml of methylene chloride. The compound 32 (1.30 g) dispersed in 100 ml of methylene chloride was then dripped, and was stirred at room temperature for 22 hours. The reaction solution was moved into a separating funnel, and was washed with 200 ml of 10% hydrochloric acid, 200 ml of aqueous saturated sodium hydrogen carbonate solution, 200 ml of ion-exchange water, and 200 ml of saturated brine in this order. After the methylene chloride phase collected was dehydrated with magnesium sulfate, the desiccant agent was removed by filtration, and the solvent of the filtrate was distilled away under reduced pressure. The reaction mixture was purified by silica-gel column chromatography, and 2.1 g of a white solid 34 was obtained.

Synthesis of 4-(pyren-1-yl)butanoic acid 11-(3-(tritylthio)propaneamide)undecylester 36

4-(pyrene-1-yl)butanoic acid (0.218 g) 35, 0.147 g of 1-ethyl-3-(3-dimethylaminopropyl)carbodiimide hydrochloride, and 0.019 g of 4-dimethylaminopyridine were dissolved in 100 ml of methylene chloride. To this, the compound 34 (0.383 g) dissolved in 50 ml of methylene chloride was added, and was stirred at room temperature for 23 hours. After that, the reaction solution was moved into a separating funnel, and was washed with 100 ml of 10% hydrochloric acid, 100 ml of aqueous saturated sodium hydrogen carbonate solution, 100 ml of ion-exchange water, and 100 ml of saturated brine in this order. After the methylene chloride phase collected was dehydrated with sodium sulfate, the desiccant agent was removed by filtration, and the solvent of the filtrate was distilled away under reduced pressure. The reaction mixture was purified by silica-gel column chromatography, and 0.35 g of a yellow-colored solid 36 was obtained.

Synthesis of 4-(pyren-1-yl)butanoic acid 11-(3-mercaptopropaneamide)undecylester 37

The compound 36 (0.297 g) was weighed and put into a 100-ml round-bottomed flask, and 2.7 ml of trifluoroacetic acid was added to that. The solution was stirred, to obtain a brown-colored uniform solution. After 0.2 ml of triethylsilane was added to that to generate a yellow-colored precipitate, the supernatant solution was distilled away under reduced pressure. To the obtained solid, 50 ml of methylene chloride was newly added so as to dissolve the solid. The resultant was then washed with 50 ml of aqueous saturated sodium hydrogen carbonate, 50 ml of ion-exchange water, and 50 ml of saturated brine. After the methylene chloride phase collected was dehydrated with sodium sulfate, the desiccant agent was removed by filtration, and the solvent of the filtrate was distilled away under reduced pressure. The reaction mixture was purified by silica-gel column chromatography, and 0.16 g of a yellow-colored solid (the compound 37 (the compound p)) was obtained.

Next, the formation of core-shell nanoparticles having the thus obtained compound p as a ligand is described.

Tetraoctyl ammonium bromide (TOAB) (0.222 g) was put into a 500-ml conical flask, and was dissolved in 55 ml of toluene. A solution formed by dissolving 71 mg of hydrogen tetrachloroaurate (III)/tetrahydrate in 20 ml of ion-exchange water was added to that, and was stirred vigorously. After the organic phase turned yellow, the above described compound p was added to a solution formed by dissolving ½ mol of TOAB in 20 ml of toluene, and was stirred for 15 minutes. Sodium borohydride (83 mg) was then dissolved in 20 ml of water and added to that. While being stirred vigorously at room temperature, the resultant was reacted overnight. The organic phase after the reaction was collected, and was condensed by an evaporator. While being stirred, the resultant was dripped little by little onto 100 ml of methanol, and reprecipitation of gold nanoparticles was carried out. After the stirring was continued overnight, solid components were collected by filtration with the use of a filter under reduced pressure. In this manner, approximately 0.08 g of a black-colored solid (nanoparticles NP-p) was obtained.

Figure 26:
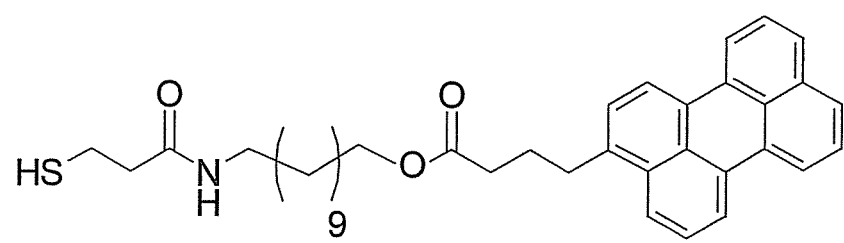
FIG. 26 is a schematic view of a compound q.
Figure 27:
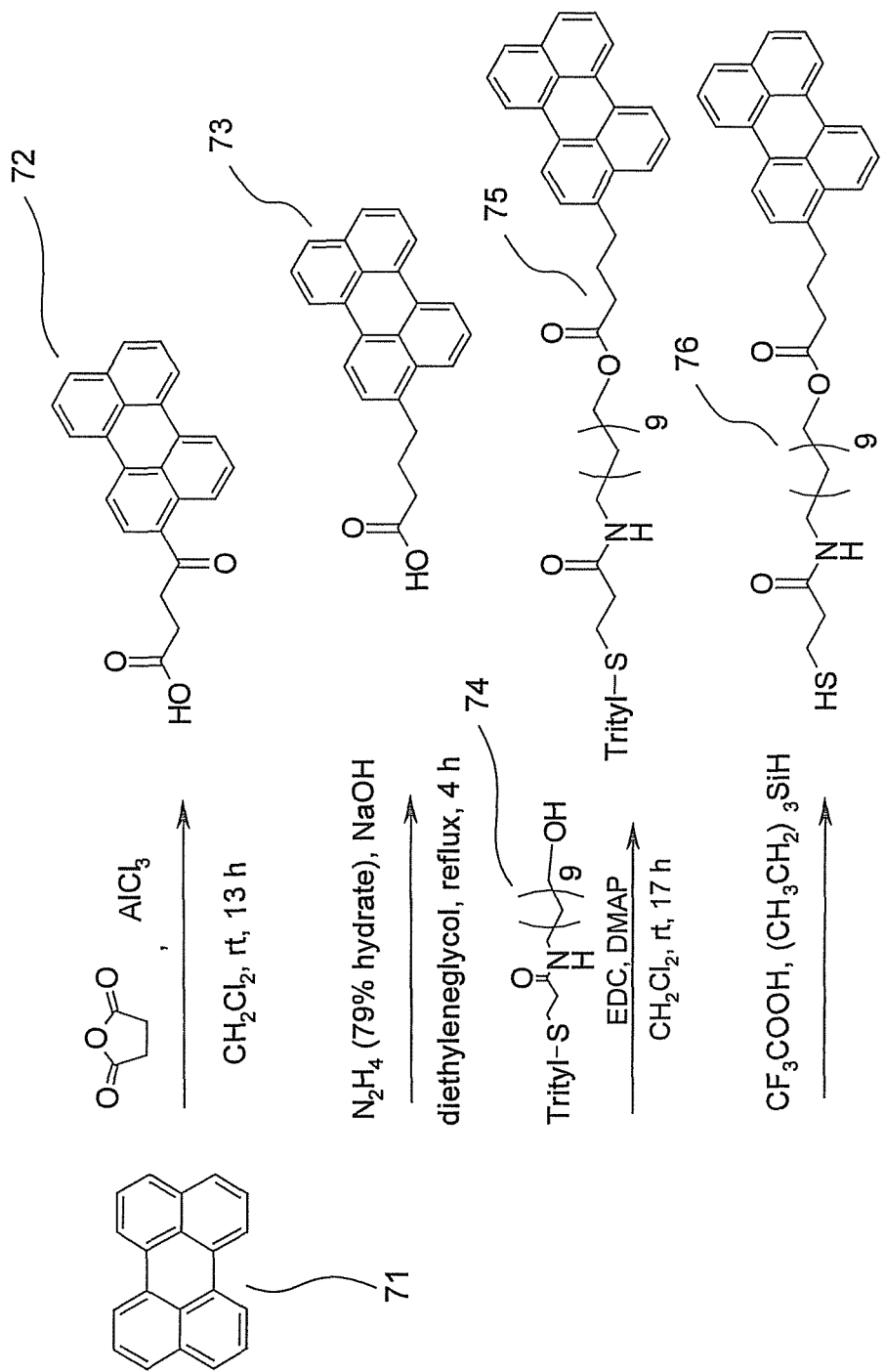
FIG. 27 is a diagram for explaining the synthesis route of the compound q.

Referring now to FIGS. 26 and 27, the formation of particles having a compound q containing perylene as the aromatic ring portion of the compound is described. This compound q is a thiol derivative having a perylene ring and an amide bond. FIG. 26 shows the structure of the compound q, and FIG. 27 illustrates the method for the synthesis of the compound q.

Synthesis of 4-(perylen-1-yl)butanoic acid 11-(3-mercaptopropaneamide)undecylester 76 (compound a)

First, a compound 72 was synthesized through a Friedel-Crafts acylation reaction between perylene 71 and succinic anhydride. After that, carbonyl was removed from the benzyl position through a Wolff-Kishiner reduction reaction, to obtain a compound 73. Further, an ester bond was formed through dehydration condensation of the compound 73 and the compound 74, to synthesize a compound 75. The trityl group was then removed through a deprotection reaction, and a compound 76 (the compound q) as the objective substance was obtained. The compound 74 was synthesized according to the Chambers' method or the like.

Synthesis of γ-oxo-4-(perylen-1-yl)butanoic acid 72

The perylene 71 (5.01 g, 19.8 mmol) and 4.34 g (43.4 mmol) of succinic anhydride were put into a 500-ml three-inlet flask, and a nitrogen substitution was performed. The substance obtained here was immersed in an ice bath. After 16.3 g (122 mmol) of aluminum chloride dispersed in 200 ml of methylene chloride was slowly dripped onto the substance, the reaction container was removed from the ice bath, and the substance was stirred at room temperature for 13 hours. After the reaction was completed, 40 ml of cooled 2M hydrochloric acid was added, followed by 30-minute stirring. The solid substance obtained here was collected by filtration. This solid substance was dispersed in 100 ml of xylene, and was heated to 140° C., to extract the impurities. After the substance was cooled slowly back to room temperature, the solid substance was collected by filtration, and was dried under reduced pressure, to obtain 6.99 g of the brownish solid substance 72.

Synthesis of 4-(perylen-1-yl)butanoic acid 73

The compound 72 (0.390 g, 1.11 mmol), 0.4 ml of 79% aqueous hydrazine, and 0.290 g (7.25 mmol) of sodium hydroxide were dissolved in 3.0 ml of diethylene glycol, followed by 90-minute refluxing in a 180-° C. oil bath. The excess hydrazine and water were distilled away, and the refluxing was continued for two more hours. After the reaction was completed, the solution was cooled back to room temperature, to precipitate a solid substance. The solid substance was collected by filtration, and was washed with ion-exchange water and 2M hydrochloric acid, followed by drying under reduced pressure. This solid substance was dispersed in 10 ml of xylene, and was heated to 140° C. In this manner, the solid substance was dissolved. After that, the substance was cooled slowly back to room temperature, to precipitate a solid substance. The solid substance generated here was collected by filtration, and was dried under reduced pressure, to obtain 0.375 g of the black solid substance 73.

Synthesis of 4-(perylen-1-yl)butanoic acid 11-(3-(tritylthio)propaneamide)undecylester 75

The compound 73 (67 mg, 0.20 mmol), 39 mg (0.21 mmol) of 1-ethyl-3-(3-dimethylaminopropyl)carbodiimide hydrochloride (EDC), and 12 mg (0.10 mmol) of 4-dimethylaminopyridine (DMAP) were dissolved in 30 ml of methylene chloride. The compound 74 (105 mg, 0.20 mmol) was added to the solution, and the solution was stirred at room temperature for 17 hours. The reacted solution was then moved into a separating funnel, and was washed twice with 30 ml of 10% hydrochloric acid, twice with 30 ml of a saturated sodium hydrogen carbonate aqueous solution, twice with 30 ml of ion-exchange water, and twice with 30 ml of saturated brine. After the collected methylene chloride phase was dehydrated with magnesium sulfate, the desiccant agent was removed by filtration, and the solvent was distilled away under reduced pressure. The reaction mixture was purified by silica gel column chromatography, and 62 mg of the yellow solid substance 75 was obtained (the yield being 36%). In the silica gel column chromatography, methylene chloride and ethyl acetate (15:1 in volume ratio)) were used as the developing solvent.

Synthesis of 4-(perylen-1-yl)butanoic acid 11-(3-mercaptopropaneamide)undecylester 76 (compound q)

The compound 75 (54 mg, 0.066 mmol) was put into a 100-ml round-bottomed flask, and 1.0 ml of trifluoroacetic acid was added, followed by stirring. As a result, a homogenous yellow-green solution was obtained. After a brown precipitation was caused by adding 0.1 ml of triethylsilane to there, the supernatant liquid was distilled away under reduced pressure. The obtained solid substance was dissolved by adding 20 ml of methylene chloride to there, and the substance obtained here was washed twice with 20 ml of a saturated sodium hydrogen carbonate aqueous solution, once with 20 ml of ion-exchange water, and once with 20 ml of saturated brine. After the collected organic phase was dehydrated with magnesium sulfate, the desiccant agent was removed by filtration, and the solvent was distilled away under reduced pressure. The reaction mixture was purified by silica gel column chromatography, to obtain 26 mg of a yellow solid substance (the compound 76 (the compound q)). The yield was 67%. In the silica gel column chromatography, the polar characteristics were gradually increased from the state only with methylene chloride, and at last, methylene chloride and ethyl acetate (5:2 in volume ratio)) were used as the developing solvent.

Production of Perylene-Containing Gold Nanoparticles (NP-q)

Figure 28:
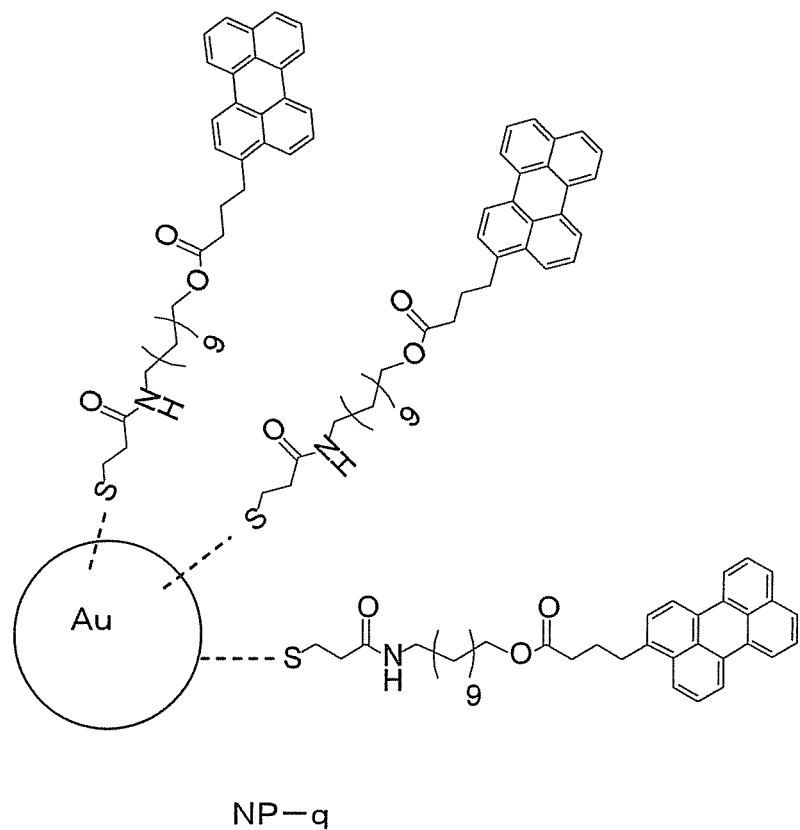
FIG. 28 is a schematic view of a core-shell nanoparticle of the substance NP-q.

Tetra-n-octylammonium bromide (85 mg, 0.16 mmol) was weighed and was put into a 200 ml conical flask. After that was dissolved in 36 ml of toluene, 27 mg (0.065 mmol) of hydrogen tetrachloroaurate (III)/tetrahydrate dissolved in 12 ml of ion-exchange water was added to that, and was stirred vigorously. The compound 76 (48 mg, 0.080 mmol) dissolved in 12 ml of toluene was then added to that and was stirred for 15 minutes. Sodium borohydride (32 mg, 0.83 mmol) dissolved in 12 ml of ion-exchange water was then added to that, and was reacted at room temperature overnight while being stirred vigorously. The reactant mixture was moved to a 500 ml brownish separating funnel, and the toluene phase was collected. The reactant mixture was then concentrated to approximately 5 ml in liquid by an evaporator having the water bath temperature set at 30° C. This concentrated liquid was dripped onto 30 ml of methanol, and was stirred at room temperature overnight. The precipitate caused here was then collected by filtration. The obtained solid substance was observed with an optical microscope. If transparent crystals of ammonium salt as the impurity were observed, the solid substance was dissolved in approximately 1 ml of chloroform, and the same reprecipitation as above was performed. This operation was repeated three times in total until the transparent crystals ceased to exist. The substance obtained here was then dried under reduced pressure, to form 26 mg of black particles (NP-q). FIG. 28 shows the structure of the particles.

Figure 29:
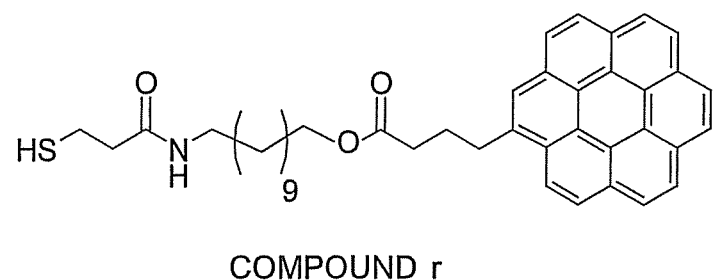
FIG. 29 is a schematic view of a compound r.
Figure 30:
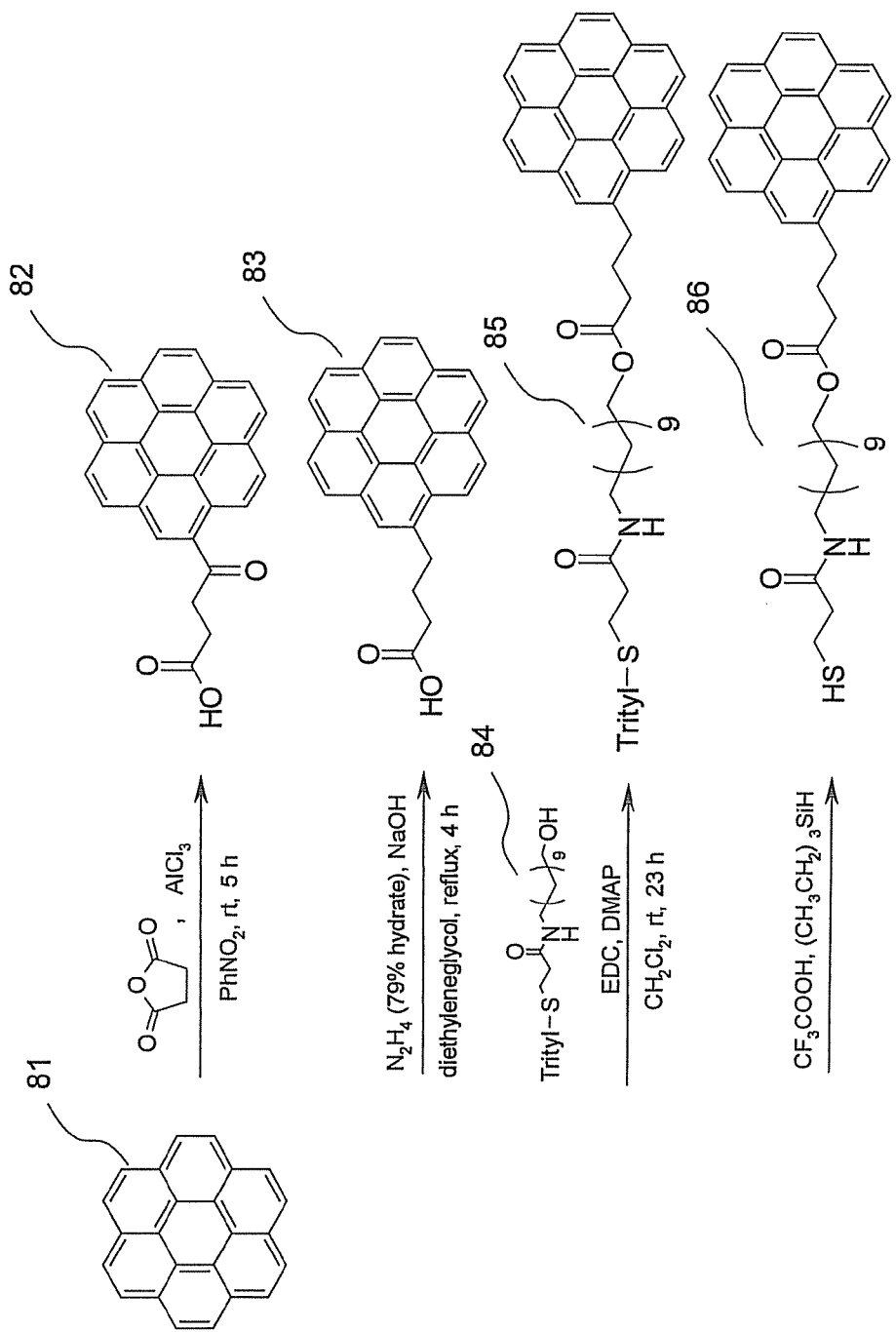
FIG. 30 is a diagram for explaining the synthesis route of the compound r.

Referring now to FIGS. 29 and 30, the formation of particles having a compound r containing coronene as the aromatic ring portion of the compound was described. FIG. 29 shows the structure of the compound r, and FIG. 30 shows the method for synthesis of the compound r.

Synthesis of γ-oxo-4-(coronen-1-yl)butanoic acid 82

The coronene 81 (0.699 g, 2.33 mmol) and 0.514 g (5.14 mmol) of succinic anhydride were put into a 100-ml two-inlet flask, and a nitrogen substitution was performed. The substance obtained here was immersed in an ice bath. After 2.80 g (21.0 mmol) of aluminum chloride dispersed in 20 ml of nitrobenzene was slowly dripped onto the substance, the reaction container was removed from the ice bath, and the substance was stirred at room temperature for 5 hours. After the reaction was completed, 10 ml of cooled 2M hydrochloric acid was added, followed by 10-minute stirring. The substance was cooled slowly down to room temperature, to precipitate a solid substance. The solid substance was collected by filtration. This solid substance was dispersed in 20 ml of xylene, and was heated to 140° C. In this manner, the solid substance was then cooled. The substance was then cooled slowly back to room temperature, to precipitate a solid substance. The solid substance obtained here was collected by filtration, and was dried under reduced pressure, to obtain 0.825 g of the yellow-green solid substance 82.

Synthesis of 4-(coronen-1-yl)butanoic acid 83

The compound 82 (0.503 g, 1.26 mmol), 0.4 ml of 79% aqueous hydrazine, and 0.462 g (11.6 mmol) of sodium hydroxide were dissolved in 3.0 ml of diethylene glycol, followed by 90-minute refluxing in a 180-° C. oil bath. The excess hydrazine and water were distilled away, and the refluxing was continued for two more hours. After the reaction was completed, the solution was cooled back to room temperature, to precipitate a solid substance. The solid substance was collected by filtration, and was washed with ion-exchange water, followed by drying under reduced pressure. This solid substance was dispersed in 10 ml of xylene, and was heated to 140° C. In this manner, the solid substance was dissolved. After that, the substance was cooled slowly back to room temperature, to precipitate a solid substance. The solid substance generated here was collected by filtration, and was dried under reduced pressure, to obtain 0.431 g of the brownish-red solid substance 83. Here, $^1$HNMR was not measured, since its product was not soluble in any deuterated solvents.

Synthesis of 4-(coronen-1-yl)butanoic acid 11-(3-(tritylthio)propaneamide)undecylester 85

The compound 83 (0.200 g, 0.517 mmol), 0.103 g (0.538 mmol) of 1-ethyl-3-(3-dimethylaminopropyl)carbodiimide hydrochloride (EDC), and 0.011 g (0.090 mmol) of 4-dimethylaminopyridine (DMAP) were dissolved in 100 ml of methylene chloride. The compound 84 (0.268 g, 0.517 mmol) was added to the solution, and the solution was stirred at room temperature for 23 hours. The solution was then moved into a separating funnel, and was washed twice with 100 ml of 10% hydrochloric acid, twice with 100 ml of a saturated sodium hydrogen carbonate aqueous solution, twice with 100 ml of ion-exchange water, and twice with 100 ml of saturated brine. After the collected methylene chloride phase was dehydrated with magnesium sulfate, the desiccant agent was removed by filtration, and the solvent of the filtrate was distilled away under reduced pressure. The reaction mixture was purified by silica gel column chromatography, and 0.168 g of the yellow solid substance 85 was obtained. The yield was 37%. In the silica gel column chromatography, methylene chloride and ethyl acetate (10:1 in volume ratio)) were used as the developing solvent.

Synthesis of 4-(coronen-1-yl)butanoic acid 11-(3-mercaptopropaneamide)undecylester 86 (compound r)

The compound 85 (0.161 g, 0.182 mmol) was put into a 100-ml round-bottomed flask, and 2.0 ml of trifluoroacetic acid was added, followed by stirring. As a result, a homogenous yellow-green solution was obtained. After a brown precipitation was caused by adding 0.5 ml of triethylsilane to there, the supernatant liquid (transparent) was distilled away under reduced pressure. The obtained solid substance was dissolved by adding 20 ml of methylene chloride to there, and the substance obtained here was washed twice with 20 ml of a saturated sodium hydrogen carbonate aqueous solution, twice with 20 ml of ion-exchange water, and twice with 20 ml of saturated brine. After the collected organic phase was dehydrated with sodium sulfate, the desiccant agent was removed by filtration, and the solvent of the filtrate was distilled away under reduced pressure. The reaction mixture was purified by silica gel column chromatography, to obtain 0.061 g of a yellow solid substance (the compound 86 (the compound r)). The yield was 52%. In the silica gel column chromatography, the polar characteristics were gradually increased from the state only with methylene chloride, and at last, methylene chloride and ethyl acetate (2:1 in volume ratio)) were used as the developing solvent.

Production of Coronene-Containing Gold Nanoparticles (NP-r)

Figure 31:
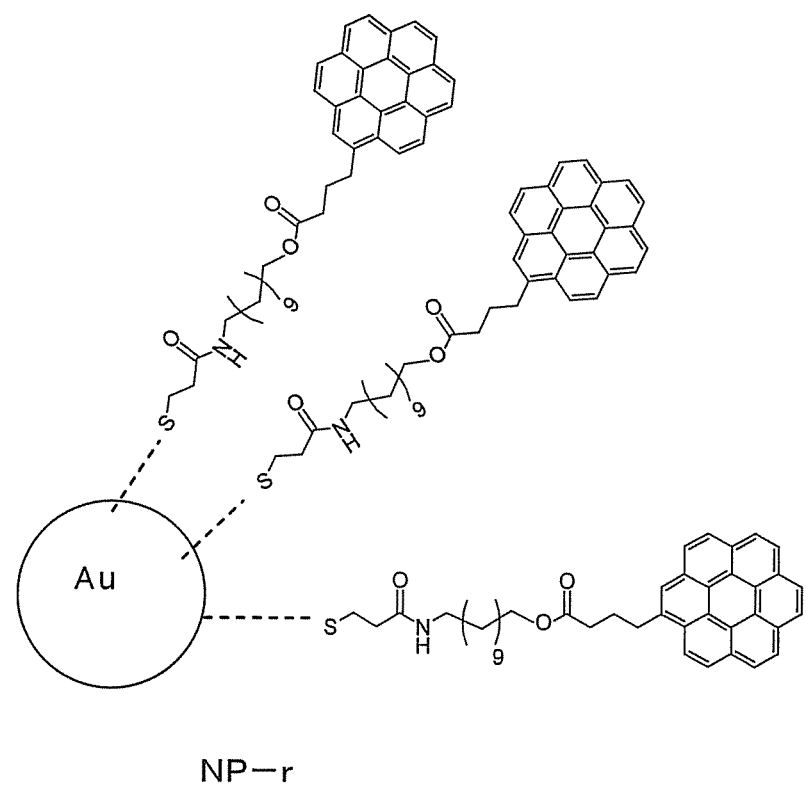
FIG. 31 is a schematic view of a core-shell nanoparticle of the substance NP-r.
Figure 32:
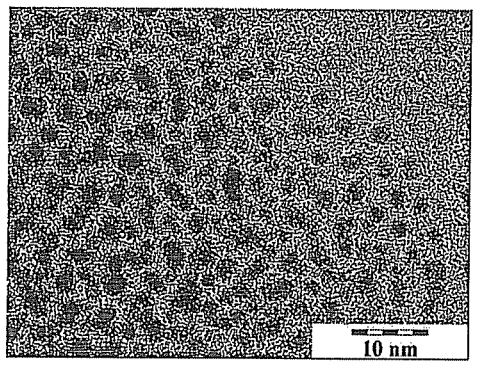
FIG. 32 shows photographs showing TEM images of particles of substances NP-q and NP-r.
Figure 32:
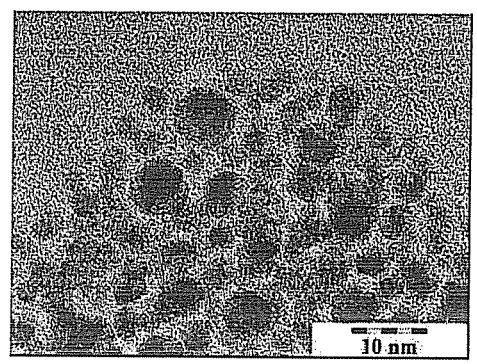

Tetra-n-octyl ammonium bromide (0.086 g, 0.158 mmol) was weighed and was put into a 200-ml conical flask. After that was dissolved in 36 ml of toluene, 0.029 g (0.070 mmol) of hydrogen tetrachloroauate (III)/tetrahydrate dissolved in 12 ml of ion-exchange water was added to that, and was stirred vigorously. The compound 86 (0.051 g, 0.079 mmol) heated and dissolved in 25 ml of toluene was then added to that and was stirred for 15 minutes. Sodium borohydride (0.031 g, 0.817 mmol) dissolved in 12 ml of ion-exchange water was then added to that, and was reacted at room temperature overnight while being stirred vigorously. The reaction mixture was moved to a 500-ml brownish separating funnel, and the toluene phase was collected. The reaction mixture was then concentrated to approximately 5 ml in liquid by an evaporator having the water bath temperature set at 30° C. This concentrated liquid was dripped onto 30 ml of methanol, and was stirred at room temperature overnight. The precipitate caused here was then collected by filtration. The obtained solid substance was observed with an optical microscope. If transparent crystals of ammonium salt as the impurity were observed, the solid substance was dissolved in approximately 5 ml of toluene, and the same reprecipitation as above was performed. This operation was repeated three times in total until the transparent crystals ceased to exist. The substance obtained here was then dried under reduced pressure, to form 66 mg of black particles (NP-r). FIG. 31 shows the structure of the particles (NP-r). FIG. 32 shows TEM images of the particles (NP-q) and the particles (NP-r).

Comparative Example

Figure 6:
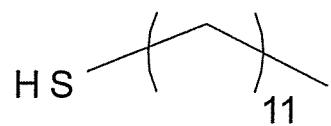
FIG. 6 is a schematic view showing a specific example of a long-chain alkanethiol derivative used as a ligand in a comparative example.
Figure 7:
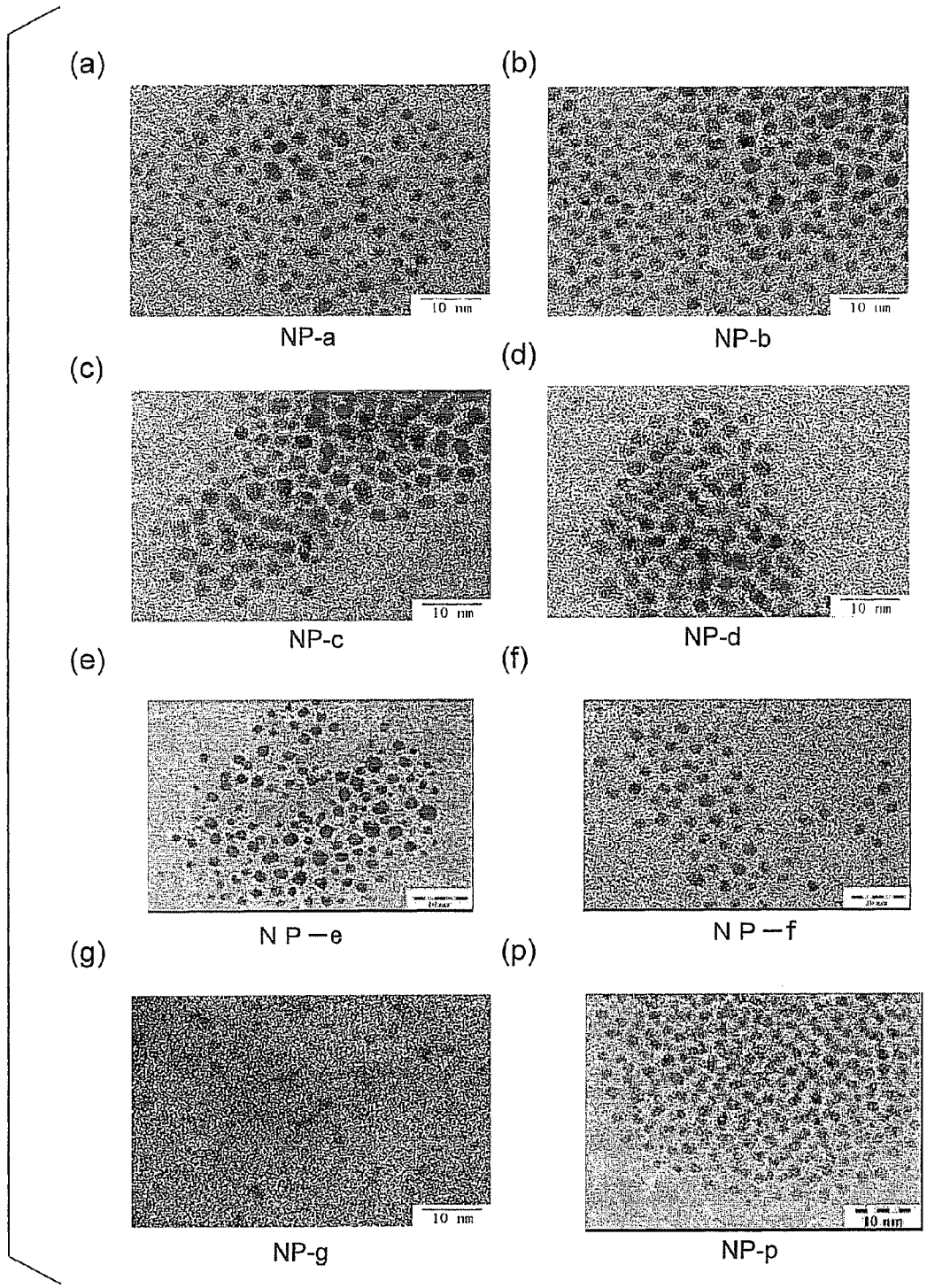
FIGS. 7(a) through 7(g) and 7(p) are photographs showing TEM images of core-shell nanoparticles of substances NP-a through NP-g and substance NP-p.

As a comparative example, core-shell particles using normal-1-dodecanethiol (hereinafter also referred to as the compound g), manufactured by Wako Pure Chemical Industries, Ltd., were formed in the same manner as in the above described cases, to obtain 0.1 g of black-colored particles. FIG. 6 shows the chemical formula for the compound g.

Hereinafter, the core-shell nanoparticles will be referred to as follows:

the black solid obtained from the thiol of the compound a will be referred to as NP-a (Example 1);

the black solid obtained from the thiol of the compound b will be referred to as NP-b (Example 2);

the black solid obtained from the thiol of the compound c will be referred to as NP-c (Example 3);

the black solid obtained from the thiol of the compound d will be referred to as NP-d (Example 4);

the black solid obtained from the thiol of the compound e will be referred to as NP-e (Example 5);

the black solid obtained from the thiol of the compound f will be referred to as NP-f (Example 6);

the black solid obtained from the thiol of the compound p will be referred to as NP-p (Example 7);

the black solid obtained from the thiol of the compound g will be referred to as NP-g (Comparative Example);

the black solid obtained from the thiol of the compound q will be referred to as NP-q (Example 8); and the black solid obtained from the thiol of the compound r will be referred to as NP-r (Example 9).

Figure 23:
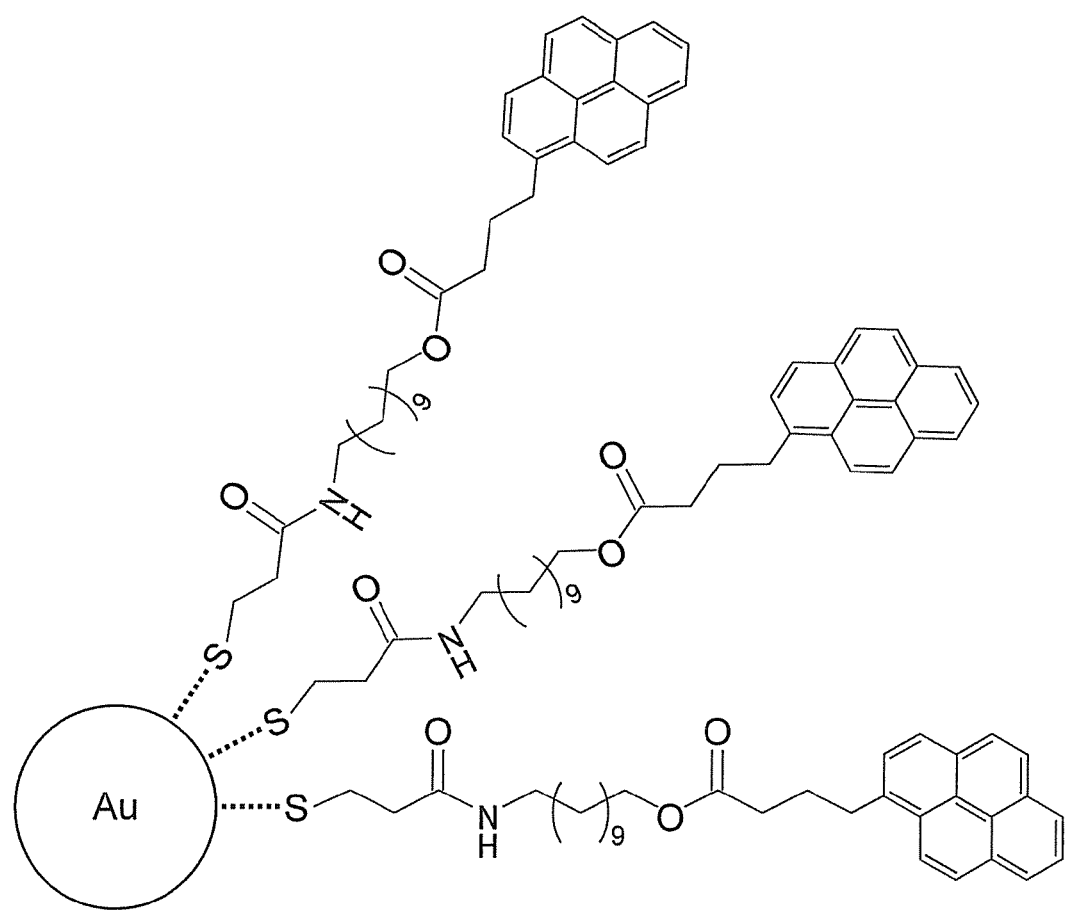
FIG. 23 is a schematic view of a core-shell nanoparticle of the substance NP-p.

FIGS. 7(a) through 7(g) and FIG. 7(p) show TEM images of the core-shell nanoparticles of the substances NP-a through NP-g and the substance NP-p obtained in the above described manner. FIGS. 8 through 14 are schematic views of the core-shell nanoparticles of the substances NP-a through NP-g. FIG. 23 is a schematic view of the core-shell nanoparticles of the substance NP-p.

Figure 15:
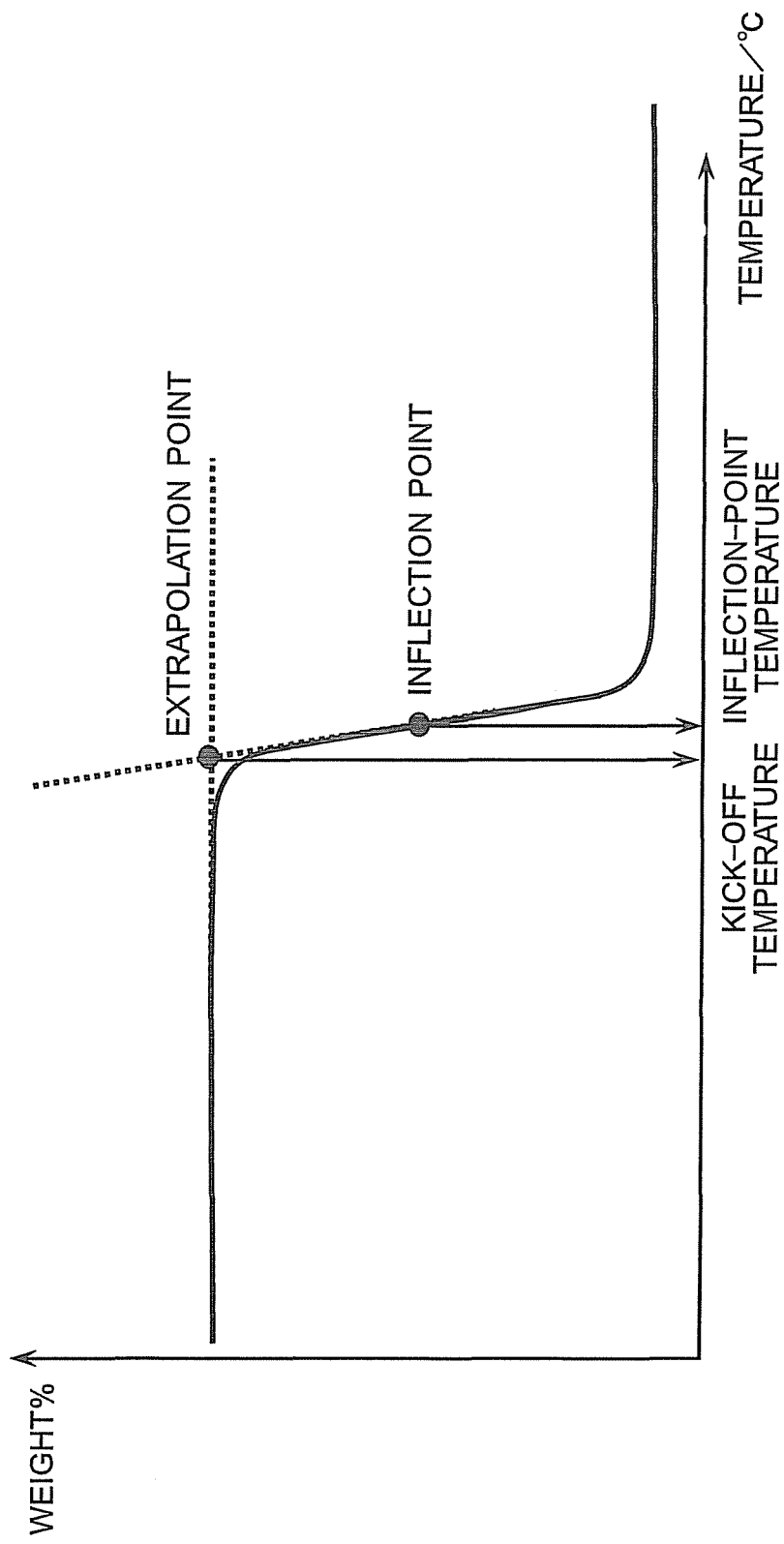
FIG. 15 is a diagram for explaining the method of determining a "kick-off" temperature.
Figure 16:
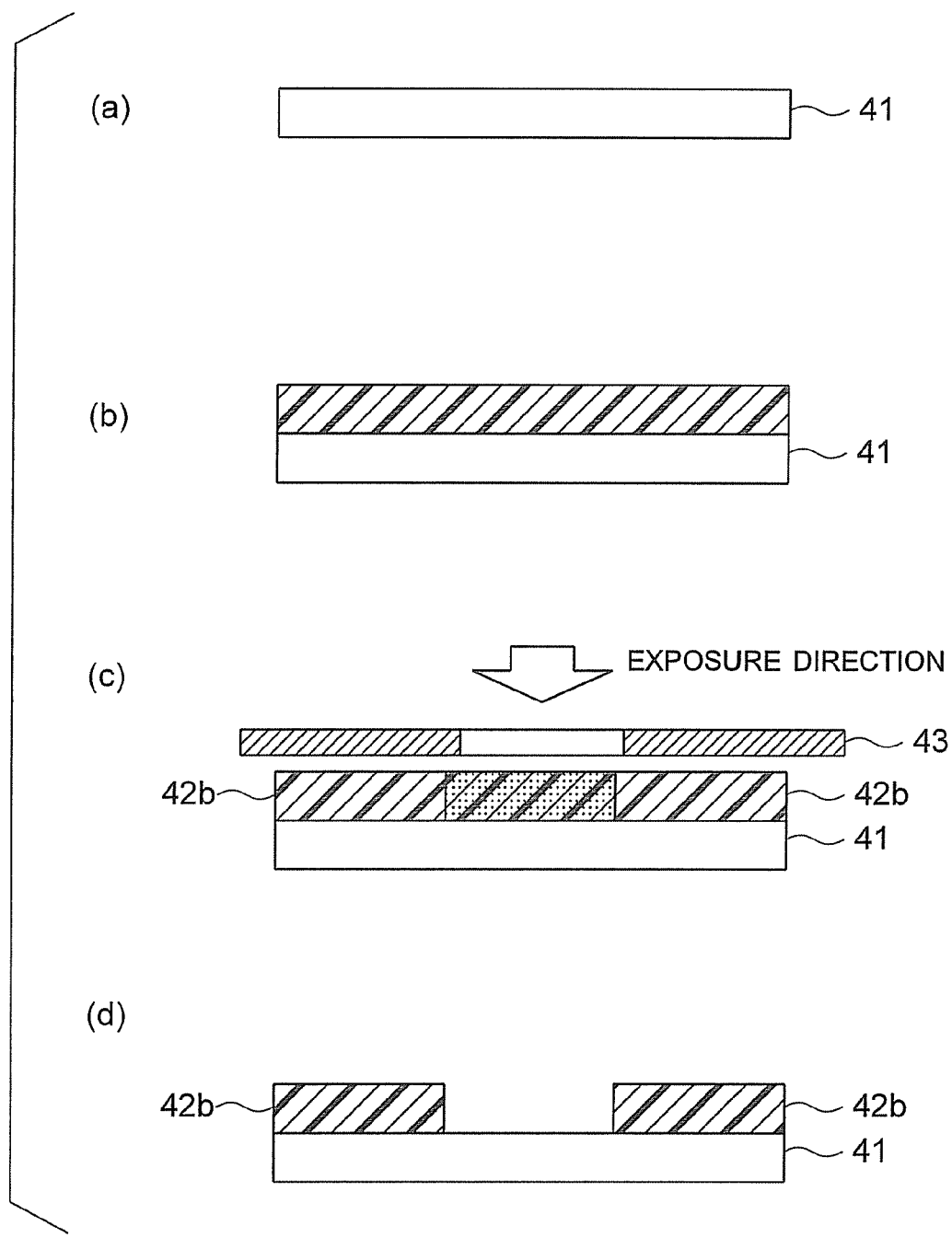
FIGS. 16(a) through 16(d) are cross-sectional views illustrating the procedures for forming a near-field optical waveguide.
Figure 17:
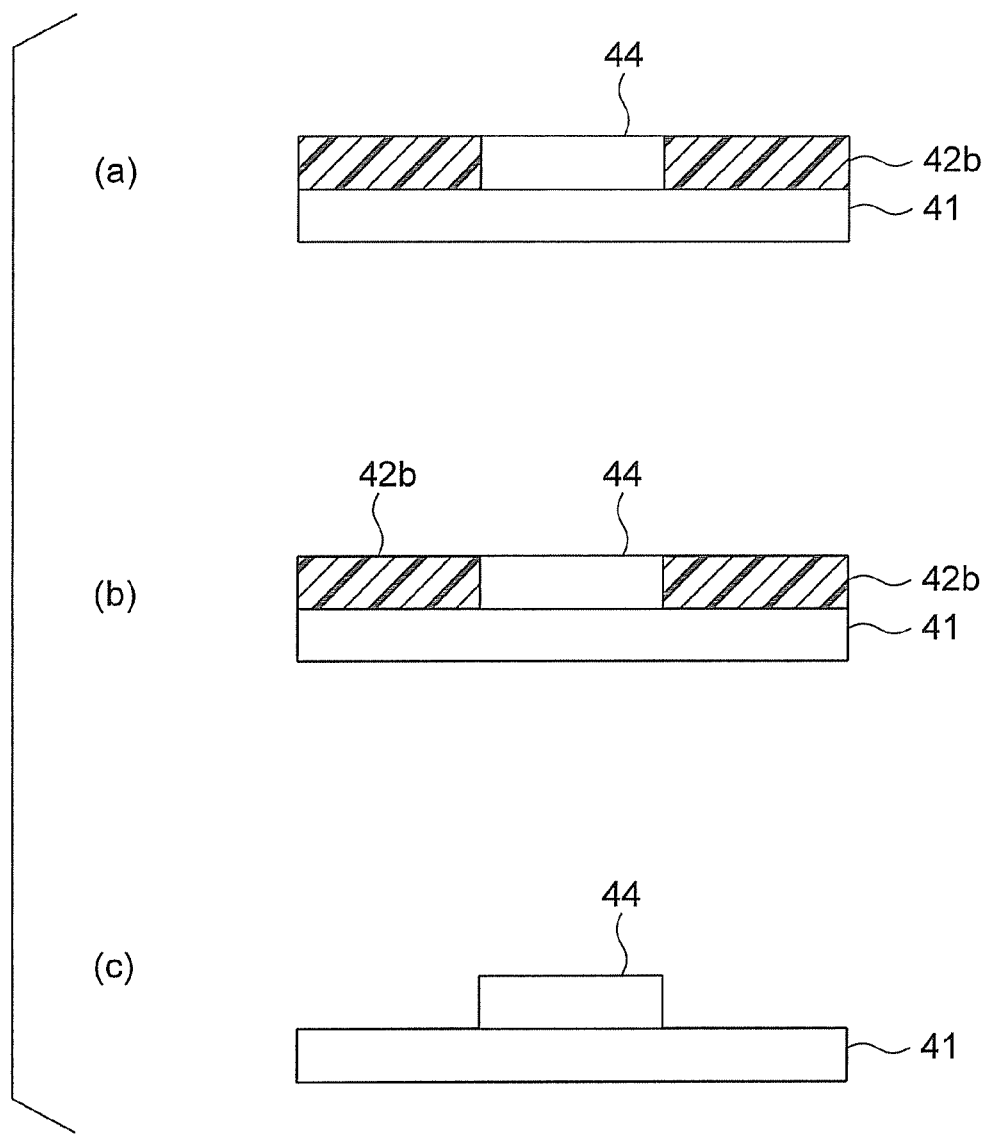
FIGS. 17(a) through 17(c) are cross-sectional views illustrating the procedures for forming a near-field optical waveguide.

Thermal analysis was carried out on the core-shell nanoparticles of the substances NP-a through NP-g and the substance NP-p through the substance NP-r. This thermal analysis was conducted with the use of a differential thermogravimetric simultaneous measuring apparatus TG/DTA6300 (manufactured by SII) in a nitrogen gas stream (150 ml/minute) so as to avoid influence of the oxygen in the air. As shown in FIG. 15, the "kick-off" temperature was determined as the temperature at the intersection point obtained by extrapolating the tangent line between the linear portion of the base line prior to a weight decrease and the inflection point of the transition region.

TABLE 1

Kick-off temperature for gold nanoparticles

| | abbreviation for gold nanoparticles | kick-off temperature | inflection-point temperature |
|---|---|---|---|
| Comparative Example | NP-g | 249 | 271 |
| Example 1 | NP-a | 253 | 290 |
| Example 2 | NP-b | 277 | 314 |
| Example 3 | NP-c | 279 | 312 |
| Example 4 | NP-d | 280 | 312 |
| Example 5 | NP-e | 298 | 341 |
| Example 6 | NP-f | 310 | 355 |
| Example 7 | NP-p | 390 | 430 |
| Example 8 | NP-q | 397 | 435 |
| Example 9 | NP-r | 417 | 450 |

The endothermic peaks and exothermic peaks were then measured in thermal analysis measurement with the use of a differential scanning calorimetry analyzer DSC6200 (manufactured by SIT). This analysis was conducted in a nitrogen gas stream (150 ml/minute) so as to avoid influence of the oxygen in the air. The results are shown in Table 2.

TABLE 2

Endothermic peak and exothermic peak for gold nanoparticles

| | abbreviation for gold nanoparticles | endothermic peak | exothermic peak |
|---|---|---|---|
| Comparative Example | NP-g | None | 239 |
| Example 1 | NP-a | None | 253 |
| Example 2 | NP-b | None | 257 |

TABLE 2-continued

Endothermic peak and exothermic peak for gold nanoparticles

| | abbreviation for gold nanoparticles | endothermic peak | exothermic peak |
|---|---|---|---|
| Example 3 | NP-c | None | 262 |
| Example 4 | NP-d | None | None |
| Example 5 | NP-e | None | 236 |
| Example 6 | NP-f | 127 | 256 |
| Example 7 | NP-p | 90 | 240 |
| Example 8 | NP-q | 140, 144 | 249 |
| Example 9 | NP-r | 118, 152 | 252 |

As can be seen from Tables 1 and 2, endothermic peaks are observed only where the molecular structure indicating hydrogen bondings are the same as the molecular structure having interactions between p orbitals of aromatic rings (Examples 6 through 9). This energy strongly depends on the interactions between molecules, and exhibits unique stability of the compounds having hydrogen bondings and interactions between p orbitals aromatic rings.

Figure 8:
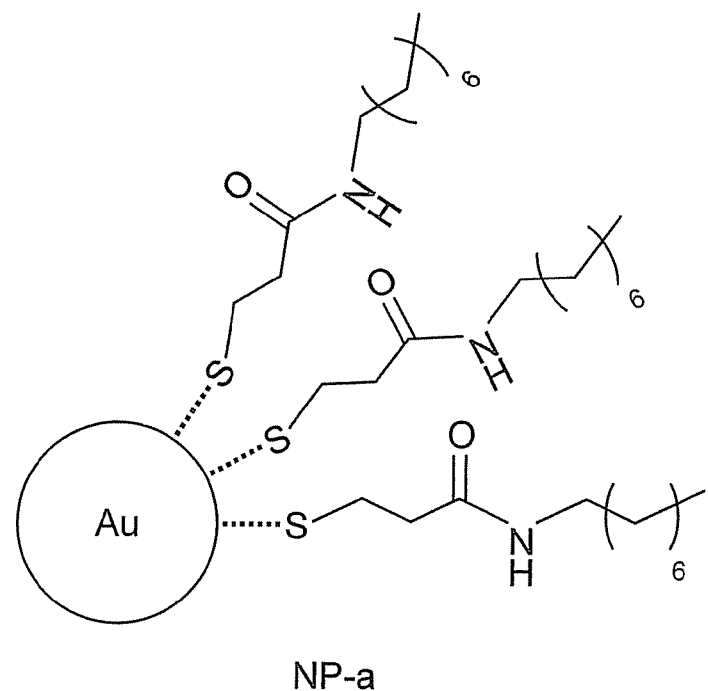
FIG. 8 is a schematic view of a core-shell nanoparticles of the substance NP-a.
Figure 9:
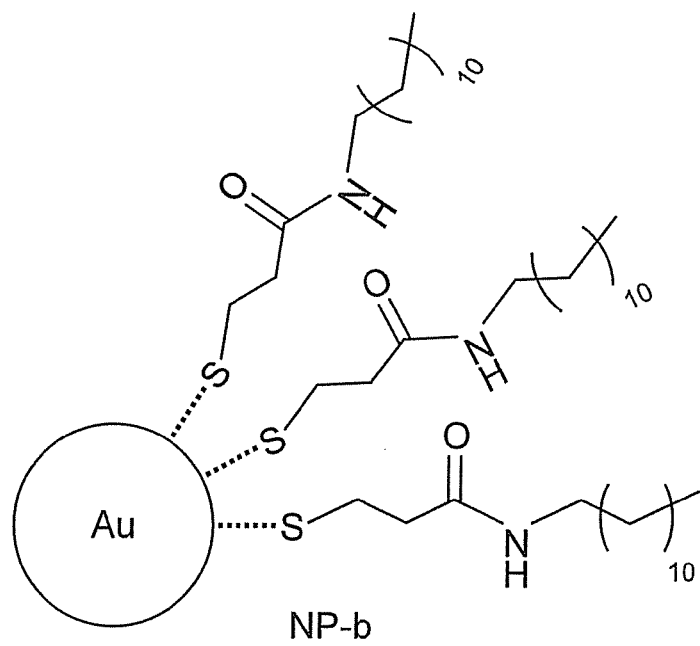
FIG. 9 is a schematic view of a core-shell nanoparticles of the substance NP-b.
Figure 10:
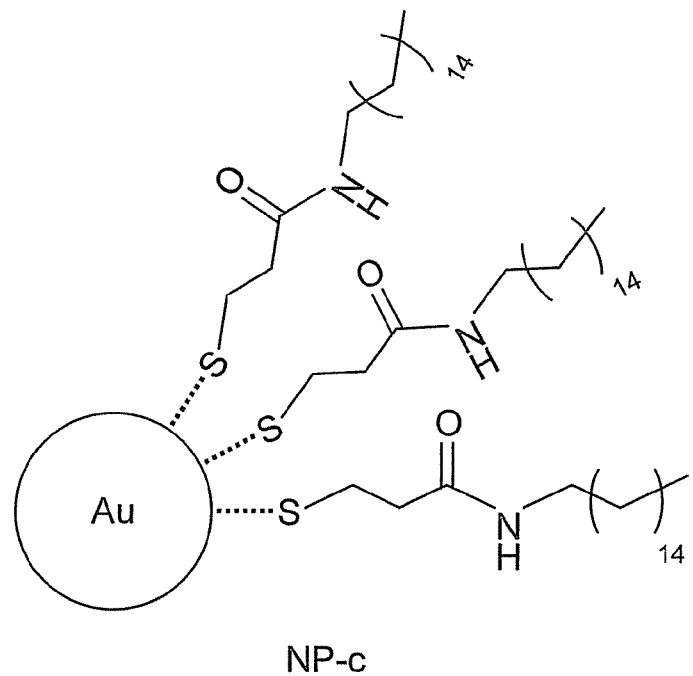
FIG. 10 is a schematic view of a core-shell nanoparticles of the substance NP-c.
Figure 11:
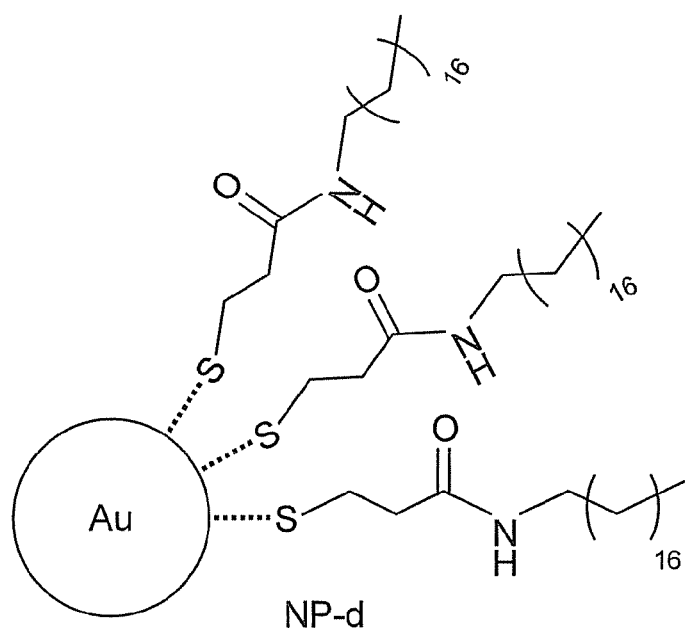
FIG. 11 is a schematic view of a core-shell nanoparticles of the substance NP-d.
Figure 12:
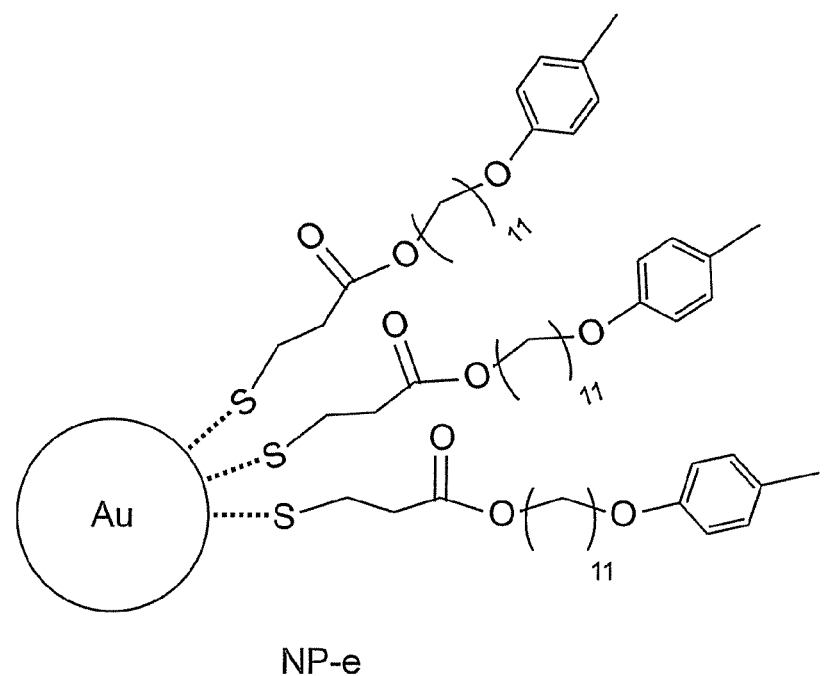
FIG. 12 is a schematic view of a core-shell nanoparticles of the substance NP-e.
Figure 13:
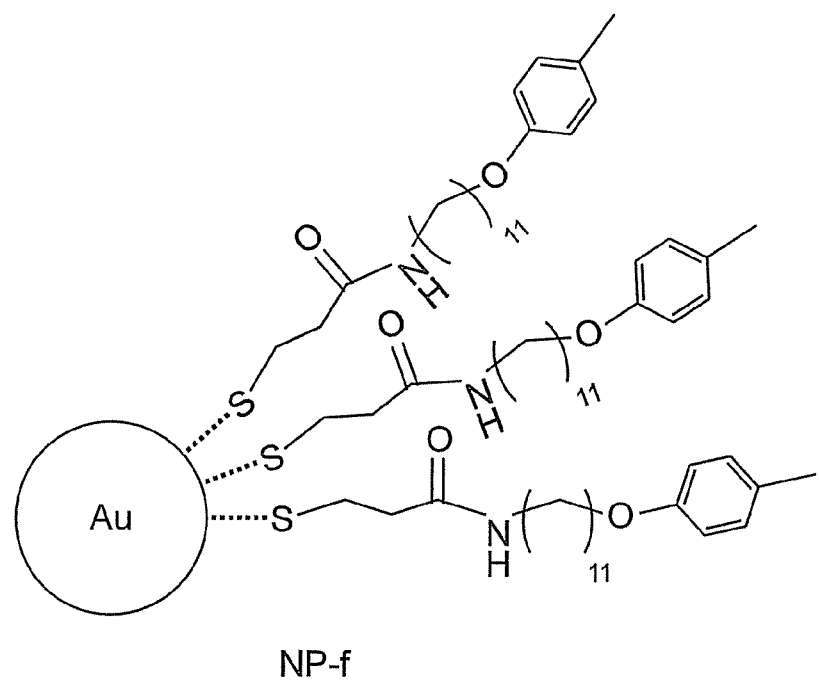
FIG. 13 is a schematic view of a core-shell nanoparticles of the substance NP-f.
Figure 14:
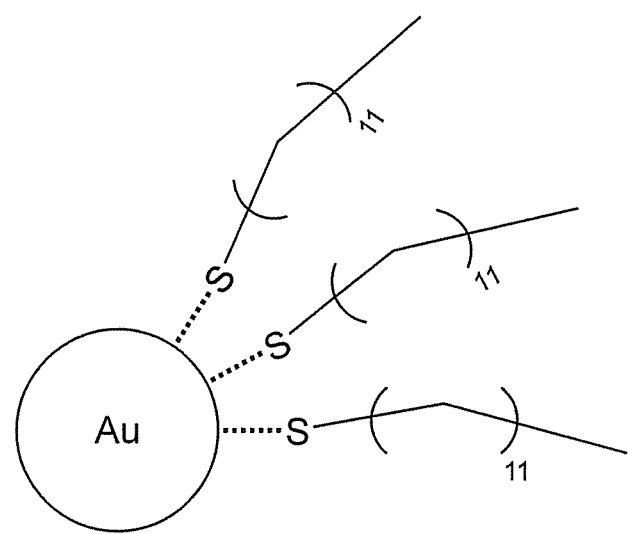
FIG. 14 is a schematic view of a core-shell nanoparticles of the substance NP-g.

As can be seen from Table 1, the kick-off temperature is 249° C. in Comparative Example. However, if N having hydrogen-bonding capability is added as in Example 1, the kick-off temperature becomes higher. Although the increase is only approximately 4° C., the molecular length differs between the substance NP-g and the substance NP-a, as shown in FIGS. 8 and 14. The kick-off temperature of the substance NP-a is higher, though having the smaller molecular length. In this manner, the influence of hydrogen bondings is very large. Furthermore, if the molecular weight is increased in the substance NP-b, the substance NP-c, and the substance NP-d, the heat resistance becomes higher by virtue of the van der Waals' force acting between alkylchains.

Also, in each of the substances NP-e, NP-f, and NP-p, aromatic rings having the pi-electrons stacking effect is incorporated into the molecular structure, so as to further increase the heat resistance. The substance NP-f and the substance NP-p both having hydrogen bondings and the pi-pi stacking effect realize the heat resistance to temperature of 300° C. or more but 400° C. or less. Accordingly, those substances can be used in semiconductor processes.

Fluorescence Measurement of Compound p and Substance NP-p

Figure 24:
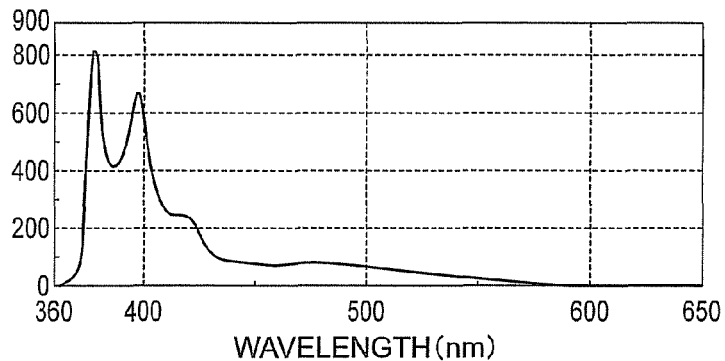
FIGS. 24(a) and 24(b) are diagrams showing the results of fluorescent measurement carried out on the compound p and the substance NP-p.
Figure 24:
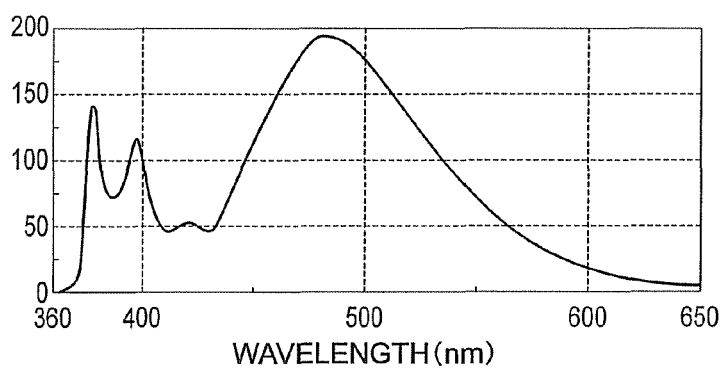

Referring now to FIGS. 24(a) and 24(b), fluorescent measurement carried out on the compound p and the substance NP-p is described.

A fluorescent measurement apparatus, JASCO FP-6500, was used, and chloroform for spectroscopic analysis that had an excitation wavelength of 345 nm and had its solvent nitrogen-bubbled for 30 minutes or longer was used. The solution concentration was 0.1 mM. With the compound p, a monomer peak derived from pyrene was obtained (FIG. 24(a)). With the substance NP-p, an excimer peak caused by interactions between pyrene rings was also obtained (FIG. 24(b)). Through the excimer peak, the pi-pi stacking of pyrene rings was confirmed. As for the number of moles of the pyrene-containing gold nanoparticles NP-p, the pyrene content was defined by measuring the decrease in the weight by thermogravimetric measurement (TG), and calculating the mol with the use of the molecular weight of the compound p from the gram weight of this organic substance.

Waveguide

Next, a waveguide is described. In an embodiment of the present invention, plasmon polaritons were used as the waveguide that propagates incident light. Plasmon polaritons are in a particular state of light that characteristically moves on a film surface. To generate plasmon polaritons, a thin film was formed by applying core-shell nanoparticles to the total reflection face of a total reflection prism, and evanescent light was emitted onto the core-shell nanoparticles by total reflection. As a result, the core-shell nanoparticles absorbed the energy of the evanescent light, and only particular wavelength was lost from the light emitted out of the prism through total reflection. Since this wavelength shifts with the angle of incident light, the existence of plasmon polaritons can be confirmed.

The same experiments as above are normally conducted with the use of Au thin films, and the experiments are of so-called Kretschmann arrangement type. For each Au thin film, it is necessary to control the film thickness by performing vapor deposition with precision, and take measures against peeling from the substrate face. The formation of a waveguide only with Au is not realistic in terms of costs. Therefore, in the present invention, a waveguide of plasmon polariton guiding type in nanoparticles formed with an organic substance and metal was manufactured. Plasmon polaritons were then generated, and the functions of the waveguide were checked.

Formation of Thin Film and Formation of Near-Field Optical Waveguide

Referring now to FIGS. 16(a) through 17(c), the formation of the above described thin film and the formation of the above described near-field optical waveguide are described.

First, as shown in FIG. 16(a), a glass substrate was prepared as a supporting substrate 41. As shown in FIG. 16(b), an i-ray resist 42 (for example, THMR-iP5720HP, manufactured by Tokyo Ohka Kogyo Co., Ltd.) was applied onto the supporting substrate 41 by a spin coating method, and prebake was performed at 90° C. As shown in FIG. 16(c), the resist 42 was exposed, with the use of a photomask 43 having a line mask pattern (the line width being 3 μm). After postbake was performed at 110° C., the exposed portion 42a was removed with a developing solution (such as aqueous tetramethyl ammonium hydroxide solution), and the unexposed portions 42b remained on (FIG. 16(d)).

Figure 18:
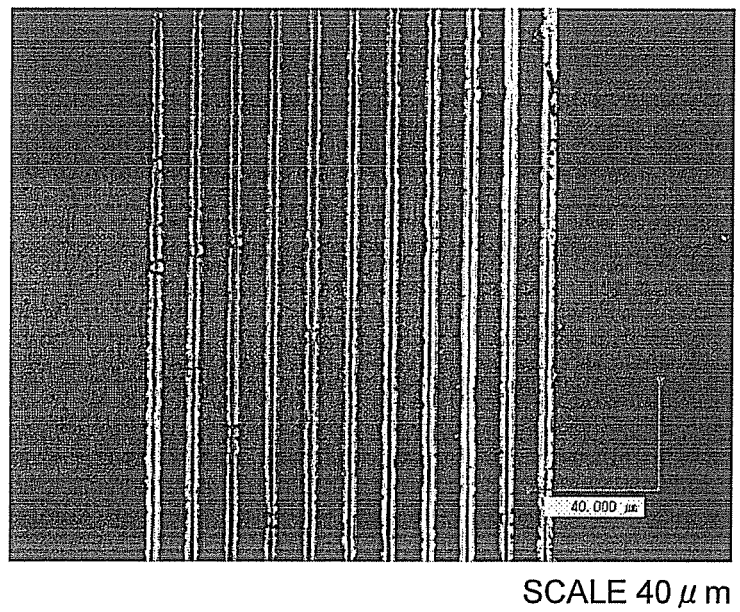
FIG. 18 is a photograph showing a wiring pattern of the near-field optical waveguide formed.

Core-shell Au nanoparticles 44 of the above described embodiment (such as NP-a) of the present invention were dissolved in dichloromethane or toluene, and a film was formed by spin coating performed at 1000 rpm (FIG. 17(a)). After 30-minute drying was performed at 40° C., the resist 42b was exposed through overall exposure (FIG. 17(b)). The resist 42b was then immersed in an ethanol solution, and was removed (FIG. 17(c)). The wiring pattern shown in FIG. 18 was formed in the above described manner, to obtain a waveguide. A wiring pattern was also formed on each of the substances NP-b through NP-g in the same manner as above, to obtain a waveguide.

Optical Measurement

Figure 19:
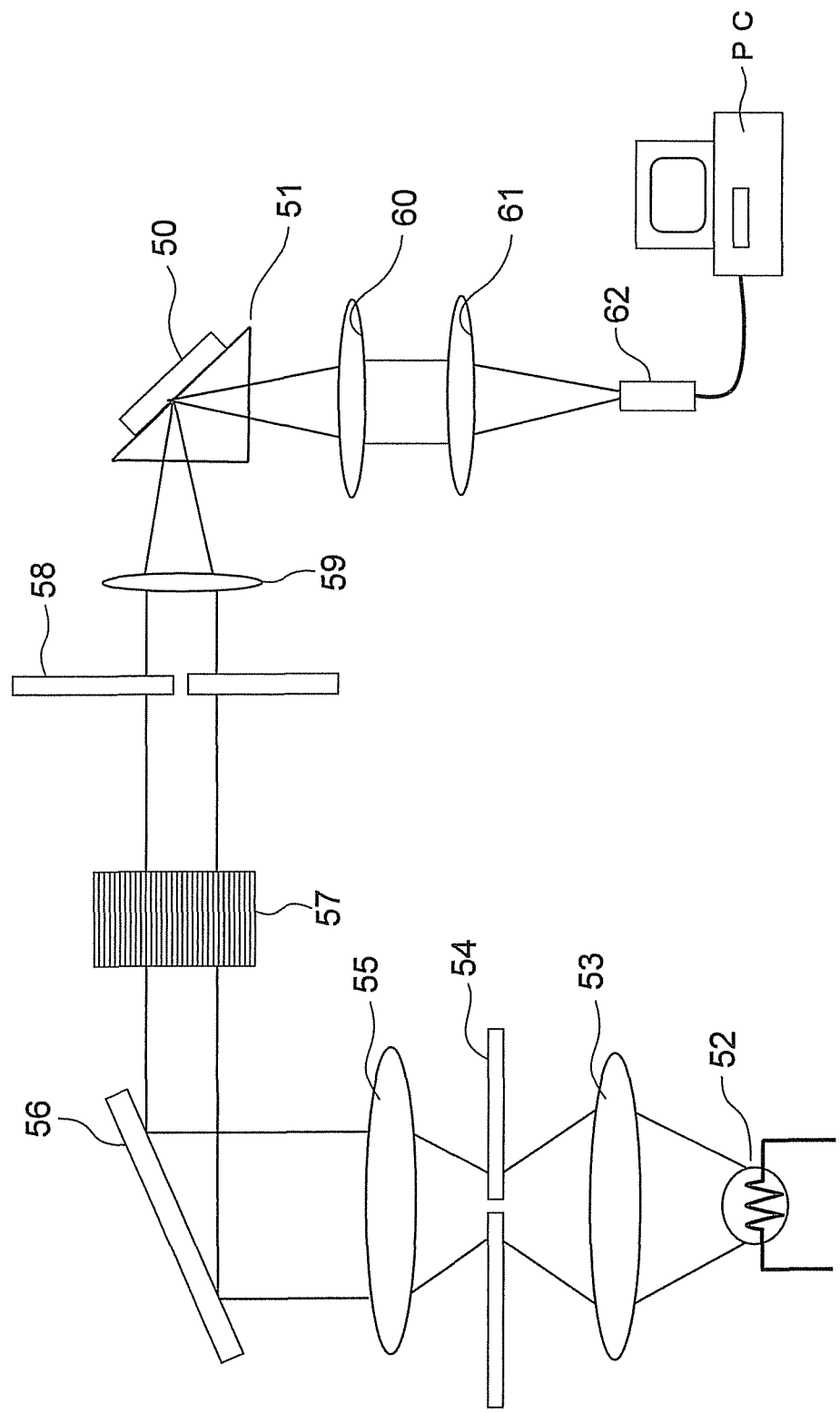
FIG. 19 is a diagram showing the optical system that measures the characteristics of the near-field optical waveguide.
Figure 20:
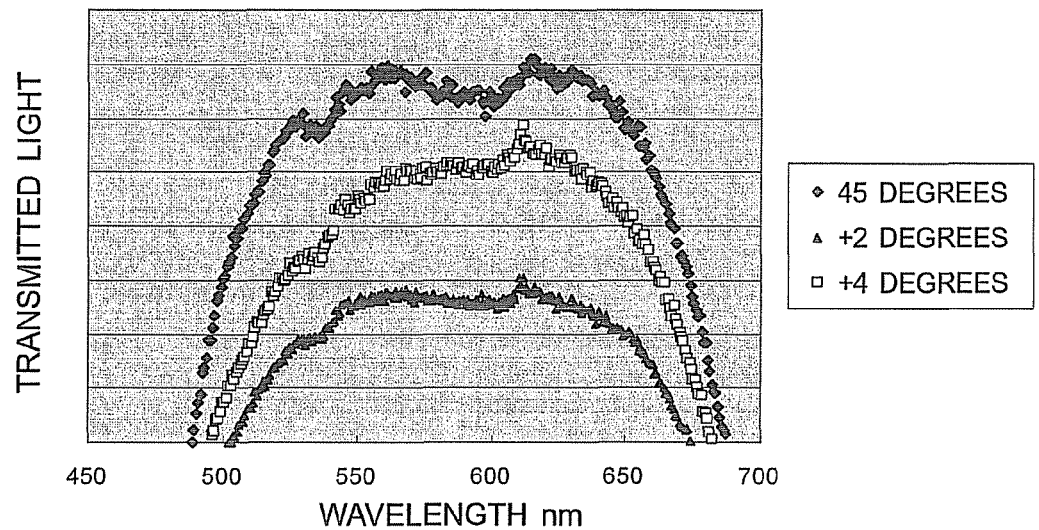
FIG. 20 is a diagram showing the characteristics of the near-field optical waveguide of an embodiment measured with the optical system shown in FIG. 19.

The above described, core-shell Au nanoparticles (such as the substance NP-e) were dissolved in dichloromethane or toluene, and were applied onto a rectangular prism 51 made of BK7 by a spin coating method at 1000 rpm. In this manner, a measurement sample 50 of a waveguide having the wiring pattern shown in FIG. 18 was formed. With the use of this measurement sample 50, the optical system shown in FIG. 19 was constructed. Light emitted from a halogen lamp 52 was narrowed to 1 mm through a lens 53, a pinhole 54, a lens 55, a mirror 56, a polarizer 57, a pinhole 58, and a lens 59, and then entered the rectangular prism 51. Total reflection at 45 degrees was conducted on the face of the prism 51 on which the measurement sample 50 was to be formed, and the reflected light was guided into an optical fiber 62 via lenses 60 and 61. The absorption data at each wavelength was stored into a personal computer PC. FIG. 20 shows the absorption data. As shown in FIG. 20, characteristic absorption was seen at around 600 nm. The angle of the prism was rotated twice, and the absorption was observed. The angle was further rotated twice, and the absorption was observed. As a result, the absorption peak shifted to the long-wavelength side. Through this measurement, generation of plasmon polaritons was confirmed.

As described above, this embodiment can provide a near-field optical waveguide that is formed with core-shell Au nanoparticles having heat resistance, and includes a particle layer to serve as an interconnect layer through which plasmon polariton is transmitted. Also, this embodiment can provide a near-field optical waveguide that is formed with the particles of Examples 8 and 9, and includes a particle layer to serve as an interconnect layer through which plasmon polariton is transmitted. The particle layers formed with the particles of Examples 7, 8, and 9 exhibit the fluorescence emission spectra by excimer excitation. The compounds contained in the particles of Examples 7, 8, and 9 are expressed by the following chemical formulas:

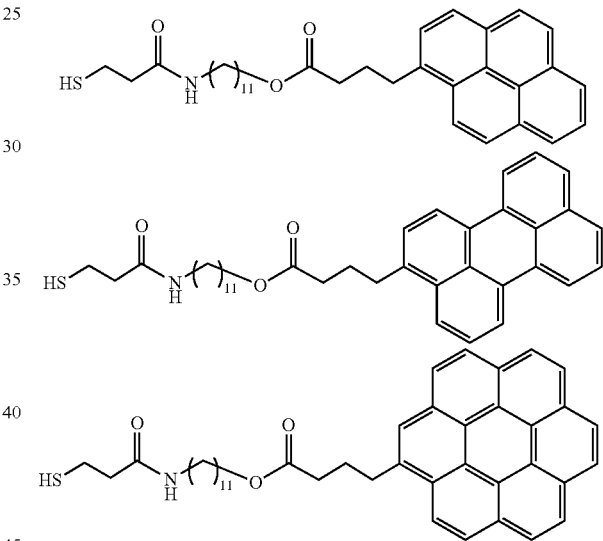

What is claimed is:

1. A particle comprising:
   a metal; and
   a compound provided as a ligand of the metal, and containing a thiol group, an amide bond, and alkylene, or containing a thiol group, carboxylato, and alkylene in a molecule,
   wherein the compound has one of the following structures:

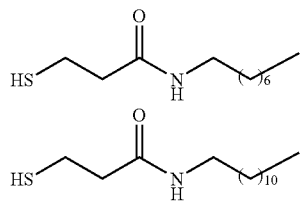

-continued

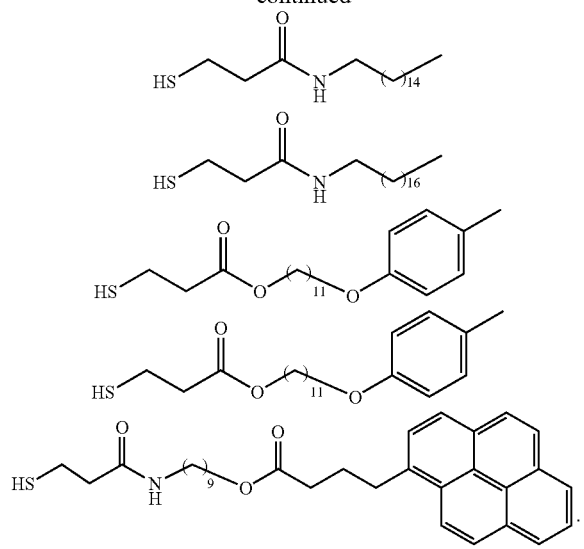

2. A particle comprising:
a metal; and
a compound containing a hydrogen-bonding forming group, an absorption group different from the hydrogen-bonding forming group, and an aromatic ring,
wherein the compound has one of the following structures:

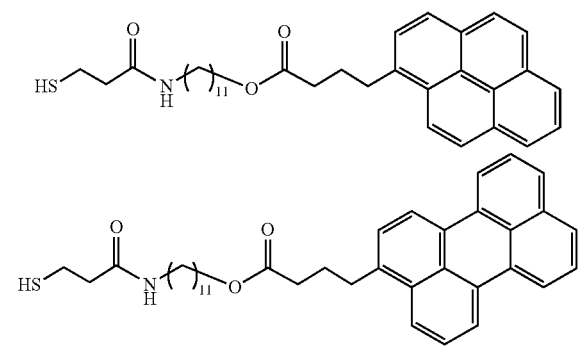

-continued

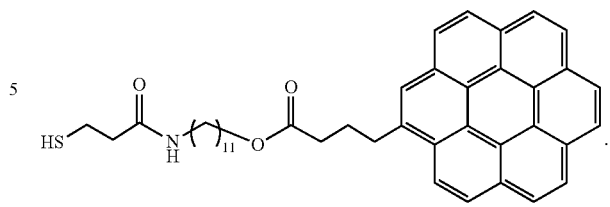

3. A particle comprising:
a metal; and
a compound containing a hydrogen-bonding forming group, an absorption group different from the hydrogen-bonding forming group, and an aromatic ring,
wherein the compound has one of the following structures:

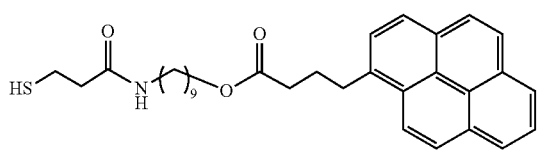

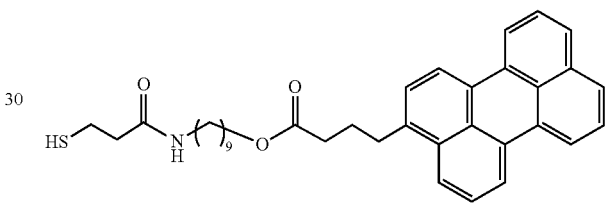

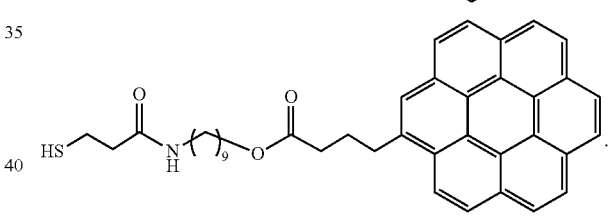

* * * * *